(12) United States Patent
Fox

(10) Patent No.: US 6,169,093 B1
(45) Date of Patent: Jan. 2, 2001

(54) QUINOLINE AND QUINAZOLINE COMPOUNDS USEFUL IN THERAPY, PARTICULARLY IN THE TREATMENT OF BENIGN PROSTATIC HYPERPLASIA

(75) Inventor: David Nathan Abraham Fox, Sandwich (GB)

(73) Assignee: Pfizer Inc., New York, NY (US)

(*) Notice: Under 35 U.S.C. 154(b), the term of this patent shall be extended for 0 days.

(21) Appl. No.: 09/341,228

(22) PCT Filed: Jan. 6, 1998

(86) PCT No.: PCT/EP98/00143

§ 371 Date: Jul. 7, 1999

§ 102(e) Date: Jul. 7, 1999

(87) PCT Pub. No.: WO98/30560

PCT Pub. Date: Jul. 16, 1998

(30) Foreign Application Priority Data

Jan. 11, 1997 (GB) .................................................. 9700504

(51) Int. Cl.⁷ ....................... A61K 31/517; C07D 239/72
(52) U.S. Cl. ............................ 514/259; 544/283; 544/292; 544/293
(58) Field of Search ..................................... 544/283, 284, 544/292, 293; 514/259

(56) References Cited

U.S. PATENT DOCUMENTS 4,026,894 * 5/1977 Winn et al. ........................ 260/256.4

FOREIGN PATENT DOCUMENTS

| 0100200 | 2/1984 | (EP) | ............................ A61K/31/495 |
| 2171997 | 9/1986 | (GB) | ............................ A61K/31/495 |
| 95/25726 * | 3/1995 | (WO) . | |
| WO9525726 | 9/1995 | (WO) | ............................ C07D/239/95 |
| WO9723462 | 7/1997 | (WO) | ............................ A61K/31/47 |

OTHER PUBLICATIONS

Hieble et al., "α– and β–Adrenoceptors: From The Gene To The Clinic. 1. Molecular Biology And Adrenoceptor Sub-classification," *J. Med. Chem.*, 38(18), pp. 3415–3444 (1995).

* cited by examiner

Primary Examiner—Mukund J. Shah
Assistant Examiner—Sudhaker B. Patel
(74) Attorney, Agent, or Firm—Peter C. Richardson; Gregg C. Benson; Todd M. Crissey

(57) ABSTRACT

Compounds of formula I,

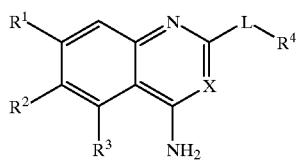

wherein
$R^1$ represents $C_{1-4}$ alkoxy optionally substituted by one or more fluorine atoms;
$R^2$ represents H or $C_{1-6}$ alkoxy optionally substituted by one or more fluorine atoms;
$R^3$ represents a 5- or 6-membered heterocyclic ring, the ring being optionally substituted;
$R^4$ represents a 4-, 5-, 6-, or 7-membered heterocyclic ring, the ring being optionally fused to a benzene ring or a 5- or 6-membered heterocyclic ring, the ring system as a whole being optionally substituted;
X represents CH or N; and
L is absent,
or represents a cyclic group of formula Ia,

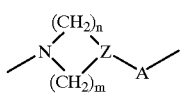

or represents a chain of formula Ib,

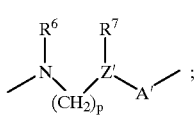

and pharmaceutically acceptable salts thereof, are useful in therapy, in particular in the treatment of benign prostatic hyperplasia.

11 Claims, No Drawings

QUINOLINE AND QUINAZOLINE COMPOUNDS USEFUL IN THERAPY, PARTICULARLY IN THE TREATMENT OF BENIGN PROSTATIC HYPERPLASIA

This invention relates to novel compounds useful in therapy, particularly in the treatment of benign prostatic hyperplasia.

International Patent Application WO 89/05297 discloses a number of substituted quinazoline compounds which are indicated as inhibitors of gastric acid secretion.

International Patent Application WO 97/23462 (published after the priority date of this application) discloses quinoline and quinazoline compounds having a 5-phenyl substituent. The compounds are indicated in the treatment of benign prostatic hyperplasia.

According to the present invention, there is provided a compound of formula I,

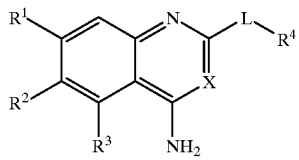

wherein
 $R^1$ represents $C_{1-4}$ alkoxy optionally substituted by one or more fluorine atoms;
 $R^2$ represents H or $C_{1-6}$ alkoxy optionally substituted by one or more fluorine atoms;
 $R^3$ represents a 5- or 6-membered heterocyclic ring containing at least one heteroatom selected from N, O and S, the ring being optionally substituted by one or more groups selected from halogen, $C_{1-4}$ alkoxy, $C_{1-4}$ alkyl and $CF_3$;
 $R^4$ represents a 4-, 5-, 6-, or 7-membered heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, $C_{1-4}$ alkyl, $C_{1-4}$ alkoxy, halogen, $CONR^8R^9$, $SO_2NR^8R^9$, $(CH_2)_bNR^8R^9$ and $NHSO_2(C_{1-4}$ alkyl), and when S is a member of the ring system, it may be substituted by one or two oxygen atoms;
 $R^8$ and $R^9$ independently represent H or $C_{1-4}$ alkyl, or together with the N atom to which they are attached they may represent a 5- or 6-membered heterocyclic ring containing at least one heteroatom selected from N, O and S;
 b represents 0, 1, 2 or 3;
 X represents CH or N; and
 L is absent,
or represents a cyclic group of formula Ia,

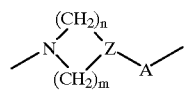

in which N is attached to the 2-position of the quinoline or quinazoline ring;

A is absent or represents CO or $SO_2$;
Z represents CH or N;
m represents 1 or 2, and in addition, when Z represents CH, it may represent 0; and
n represents 1, 2 or 3, provided that the sum of m and n is 2, 3, 4 or 5; or represents a chain of formula Ib,

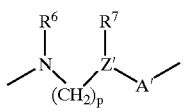

in which N is attached to the 2-position of the quinoline or quinazoline ring;
 A' and Z' have the same significance as A and Z above, respectively;
 $R^6$ and $R^7$ independently represent H or $C_{1-4}$ alkyl; and
 p represents 1, 2 or 3, and in addition, when Z' represents CH, it may represent 0;

or a pharmaceutically acceptable salt thereof (referred to together herein as "the compounds of the invention").

Pharmaceutically acceptable salts include acid addition salts, such as hydrochloride and hydrobromide salts, and phosphate salts.

Alkyl and alkoxy groups that $R^{1-4}$ may represent or include can be straight chain, branched chain, cyclic, or a combination thereof.

Preferably, $R^3$ is an aromatic ring, for example pyridinyl, pyrimidinyl, thienyl, furanyl or oxazolyl.

Heterocyclic groups that $R^4$ comprises may be saturated or unsaturated. However, it is preferred that the ring attached to L, or when L is absent, to the quinoline or quinazoline ring, is saturated.

The compounds of the invention may be optically active. In particular, they may exhibit atropisomerism about the bond joining $R^3$ to the rest of the molecule when an $R^3$ substituent is in the ortho-position of the ring. The invention includes all optical isomers of the compounds of formula I, and all diastereoisomers thereof.

Preferred groups of compounds that may be mentioned include those in which:
 (a) $R^1$ represents methoxy;
 (b) $R^2$ represents methoxy;
 (c) $R^3$ represents 2-pyridinyl or 2-pyrimidinyl;
 (d) $R^4$ comprises a saturated 6-membered N-containing ring which is fused to a benzene or pyridine ring; for example $R^4$ may be a saturated 6-membered N-containing ring which is fused to a benzene ring substituted by $NHSO_2(C_{1-4}$ alkyl);
 (e) X represents N; and
 (f) L is absent.

According to the invention, there is also provided a process for the production of a compound of the invention, which comprises:
 (a) when X represents CH, cyclizing a compound of formula X,

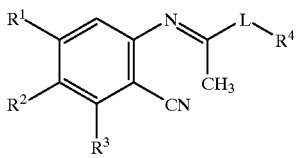

in which $R^{1-4}$ and L are as defined above;

(b) when A or A' is present, and Z or Z' represents N, reacting a compound of formula XIIIa or XIIIb, as appropriate,

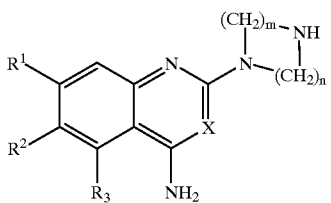

XIIIa

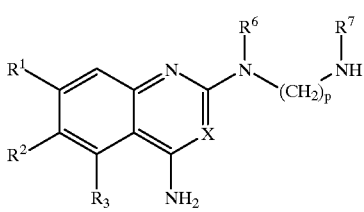

XIIIb in which $R^{1-3}$, $R^6$, $R^7$, X, m, n and p are as defined above, with a compound of formula XIV,

XIV in which $R^4$ is as defined above, A" represents CO or $SO_2$ and Lg represents a leaving group;

(c) reacting a compound of formula XVIII,

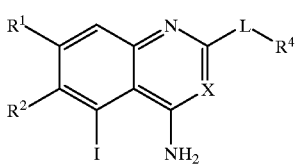

XVIII in which $R^1$, $R^2$, $R^4$, X and L are as defined above, with a compound of formula XIX,

XIX in which $R^3$ is as defined above and M represents substituted boron, zinc or tin, in the presence of a palladium catalyst;

(d) when X represents N, reacting a compound of formula XXII,

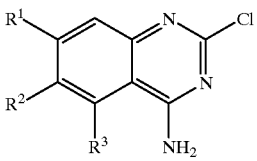

XXII in which $R^{1-3}$ are as defined above, with a compound of formula XXIIIa or XXIIIb, as appropriate,

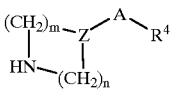

XXIIIa

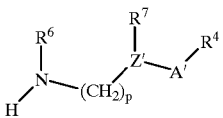

XXIIIb in which $R^4$, $R^6$, $R^7$, A, A', Z, Z', m, n and p are as defined above;

(e) when A or A' represents CO and $R^4$ comprises a nucleophilic nitrogen atom in the heterocyclic ring attached to L, reacting a compound of formula XXVIIIa or XXVIIIb, as appropriate,

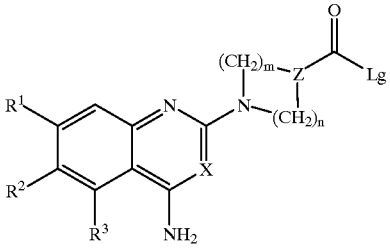

XXVIIIa

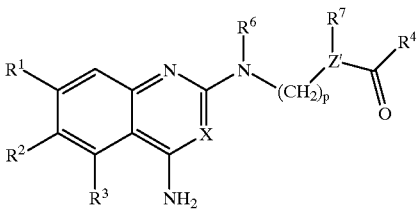

XXVIIIb in which $R^{1-3}$, $R^6$, $R^7$, X, Z, Z', m, n and p are as defined above, and Lg is a leaving group, with a compound of formula XXIX, HR$^{4a}$     XXIX in which $R^{4a}$ represents the groups defined by $R^4$ above which contain a nucleophilic nitrogen atom in the ring, this nucleophilic nitrogen atom being attached to H;

(f) conversion of a compound of formula I in which L represents a cyclic group of formula Ia, to a corresponding compound of formula I in which L represents a chain of formula Ib in which $R^6$ and $R^7$ each represent H, by the action of a strong base;

(g) when A or A' is absent and Z or Z' represents N, reacting a compound of formula XIIIa or XIIIb, as defined above, with a compound of formula XXX, $R^4$—Hal    XXX in which $R^4$ is as defined above and Hal represents a halogen atom attached to the ring; or (h) when X represents N, L is absent and $R^4$ comprises a nucleophilic nitrogen atom in the heterocyclic ring attached to the quinoline or quinazoline ring, reacting a compound of formula XXII, as defined above, with a compound of formula XXIX, as defined above; and where desired or necessary converting the resulting compound of formula I into a pharmaceutically acceptable salt or vice versa.

In process (a), the cyclization may be carried out in the presence of a strong base (for example lithium diisopropylamide) in a solvent which does not adversely affect the reaction (for example tetrahydrofuran) around room temperature and quenched with water. In a variation, it may be performed using potassium hydroxide in a solvent such as DMSO at an elevated temperature. Alternatively, it may be performed using zinc chloride in a solvent which does not adversely affect the reaction (for example tetrahydrofuran), at the reflux temperature of the solvent.

In process (b), suitable leaving groups are OH and Cl. When the compound of formula XIV is a carboxylic acid, the reaction may be carried out in the presence of conventional coupling agents [for example 1-hydroxybenz6triazole monohydrate, 1-(3-dimethylaminopropyl)-3-ethylcarbodiimide hydrochloride and 4-methylmorpholine] in a solvent which does not adversely affect the reaction (for example $CH_2Cl_2$) at or around room temperature. When the leaving group is Cl, the reaction may be carried out in a solvent which does not adversely affect the reaction (for example $CH_2Cl_2$) around 0° C.

In process (c), the palladium catalyst may be tetrakis(triphenylphosphine)palladium. M may be $B(OH)_2$, $B(CH_2CH_2)_2$, $Sn(CH_2CH_2CH_2CH_3)_3$ or ZnCl. The reaction may be carried out in a solvent which does not adversely affect the reaction (for example, when M is $B(OH)_2$, a mixture of toluene, ethanol and 1M aqueous sodium carbonate) at an elevated temperature (for example the reflux temperature of the solvent). Optionally, when M represents ZnCl or substituted Sn, copper(I) iodide may be used as a co-catalyst.

In process (d), the reaction may be carried out in a solvent which does not adversely affect the reaction (for example n-butanol) in the presence of a base (for example triethylamine) at an elevated temperature (for example 100° C.).

In process (e), suitable leaving groups include Cl. The reaction may be carried out in a solvent which does not adversely affect the reaction (for example THF) in the presence of a base (for example triethylamine) at room temperature.

The reaction may also be carried out without isolating the compound of formula XXVIIIa or XXVIIIb, by reacting a compound of formula XIIIa or XIIIb with triphosgene and a compound of formula XXIX. In this case the leaving group is —Cl. The reaction may be carried out in a solvent which does not adversely affect the reaction (for example $CH_2Cl_2$) in the presence of a base (for example triethylamine) at or around room temperature.

In process (f), suitable strong bases include lithium diisopropylamide. The reaction may be carried out in a solvent which does not adversely affect the reaction (for example THF).

In process (g), the reaction may be carried out in a solvent which does not adversely affect the reaction (for example a mixture of n-BuOH and dimethylacetamide) in the presence of a base (for example triethylamine) at an elevated temperature (for example 80° C.).

In process (h), the reaction may be carried out in a solvent which does not adversely affect the reaction (for example a mixture of n-butanol and dimethylacetamide) in the presence of a base (for example triethylamine) at an elevated temperature (for example 100° C.).

Compounds of formula X [see process (a)] may be prepared by reaction of a compound of formula XI,

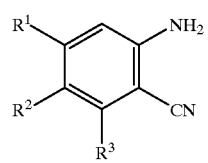

XI in which $R^{1-3}$ are as defined above, with a combination of a compound of formula XII,

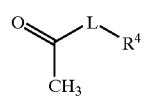

XII in which $R^4$ and L are as defined above, and phosphorous oxychloride in dichloromethane at the reflux temperature of the solvent.

Compounds of formula XIIIa or XIIIb [see process (b)] in which X represents CH may be prepared from compounds of formula XVa or XVb, as appropriate,

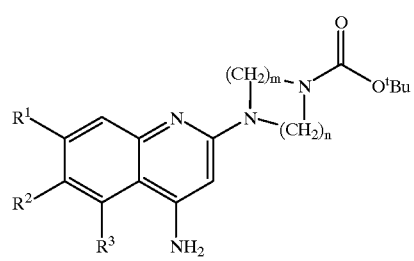

XVa

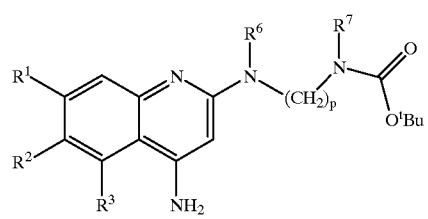

XVb in which $R^{1-3}$, $R^6$, $R^7$, m, n and p are as defined above, by bubbling HCl gas through a solution of the compound in dichloromethane.

Compounds of formula XVa or XVb may be prepared from compounds of formula XVIa or XVIb, as appropriate, XVIa

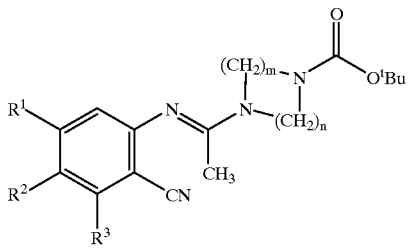

XVIb in which $R^{1-3}$, $R^6$, $R^7$, m, n and p are as defined above, by cyclization using potassium hydroxide at an elevated temperature (such as 90° C.) in DMSO, or lithium diisopropylamide in a solvent that does not adversely affect the reaction (for example tetrahydrofuran) around room temperature and quenching with water.

Compounds of formula XVIa or XVIb may be prepared by reacting a compound of formula XI, as defined above, with a compound of formula XVIIa or XVIIb, as appropriate, XVIIa XVIIb in which $R^6$, $R^7$, m, n and p are as defined above, by the method described above for producing compounds of formula X.

Compounds of formula XIIIa or XIIIb in which X represents N may be prepared by reacting a compound of formula XXII,

XXII in which $R^{1-3}$ are as defined above, with a compound of formula XXIIa or XXIIb, as appropriate, XXIIa XXIIb in which $R^6$, $R^7$, m, n and p are as defined above, using the conditions mentioned for process (d) above.

Compounds of formula XVIII [see process (c)] in which X represents CH may be prepared by cyclization of a compound of formula XX,

XX in which $R^1$, $R^2$, $R^4$ and L are as defined above, using the reaction conditions mentioned in process (a) above.

Compounds of formula XX may be prepared by reacting a compound of formula XXI,

XXI in which $R^1$ and $R^2$ are as defined above, with a compound of formula XII as defined above, using the method described above for the preparation of compounds of formula X.

Compounds of formula XVIII in which X represents N may be prepared by reacting a compound of formula XXVII,

XXVII in which $R^1$ and $R^2$ are as defined above, with a compound of formula XXIIIa or XXIIIb, as appropriate, as defined above, using the reaction conditions mentioned above for process (d).

Compounds of formula XXII [see processes (d) and (h)] may be prepared from a compound of formula XXIV,

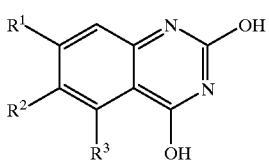
XXIV in which $R^{1-3}$ are as defined above, by reaction with $POCl_3$ and N,N-dimethylaniline, followed by treatment with ammonia.

Compounds of formula XXIV may be prepared from a compound of formula XXV,

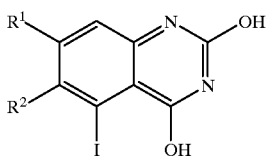
XXV in which $R^1$ and $R^2$ are as defined above, by reaction with a compound of formula XIX as defined above using the reaction conditions described above for process (c).

Compounds of formula XXV may be prepared from compounds of formula XXVI,

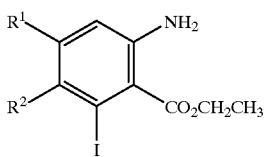
XXVI in which $R^1$ and $R^2$ are as defined above, using conventional techniques.

Compounds of formula XXII may also be prepared according to Scheme 1:

Scheme 1

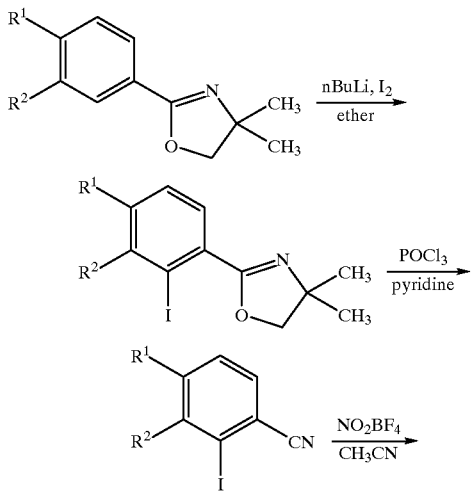

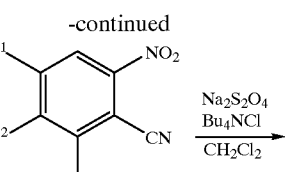

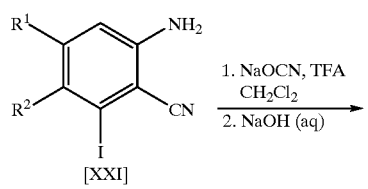
[XXI]

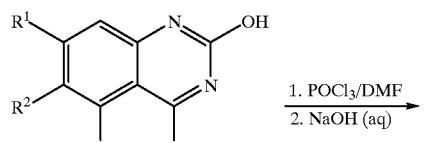

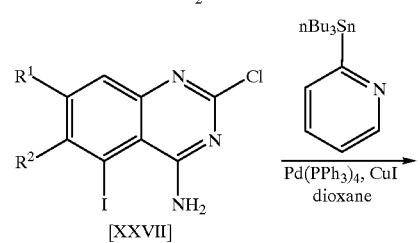
[XXVII]

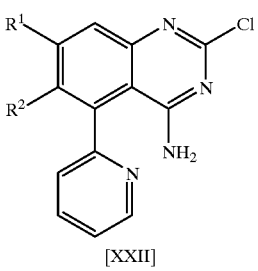
[XXII]

Compounds of formula XXVIIIa and XXVIIIb [see process (e)] in which Lg represents Cl may be prepared from compounds of formula XIIIa or XIIIb, as appropriate, by reaction with triphosgene. The reaction may be carried out in a solvent which does not adversely affect the reaction (for example $CH_2Cl_2$) in the presence of a base (for example triethylamine) at around $-10°$ C.

Compounds of formula X may also be prepared by reaction of a compound of formula XX with a compound of formula XIX using the conditions described for process (c).

Compounds of formulae XI, XII, XIV, XVIIa, XVIIb, XIX, XXI, XXIIa, XXIIb, XXIIIa, XXIIIb, XXVI, XXIX and XXX are either known or are available using known techniques, as illustrated by the Examples.

The intermediate compounds of formulae X, XIIIa, XIIIb, XXII, XXVIIIa and XXVIIIb form a further aspect of the invention.

It will be apparent to those skilled in the art that sensitive functional groups may need to be protected and deprotected during synthesis of a compound of the invention. This may be achieved by conventional techniques, for example as described in 'Protective Groups in Organic Synthesis' by T W Greene and P G M Wuts, John Wiley and Sons Inc. 1991.

The compounds of the invention are useful because they possess pharmacological activity in animals. In particular, the compounds are useful in the treatment of a number of conditions including hypertension, myocardial infarction, male erectile dysfunction, hyperlipidaemia, cardiac arrhythmia and benign prostatic hyperplasia. The latter condition is of greatest interest. Thus, according to another aspect of the invention, there is provided a method of treatment of benign prostatic hyperplasia which comprises administering a therapeutically effective amount of a compound of the invention to a patient suffering from such a disorder. The use of the compounds of the invention as pharmaceuticals, and the use of the compounds of the invention in the manufacture of a medicament for the treatment of benign prostatic hyperplasia, are also provided.

The compounds of the invention may be administered by any convenient route, for example orally, parenterally (e.g intravenously, transdermally) or rectally. The daily dose required will of course vary with the particular compound used, the particular condition being treated and with the severity of that condition. However, in general a total daily dose of from about 0.01 to 10 mg/kg of body weight, and preferably about 0.05 to 1 mg/kg, is suitable, administered from 1 to 4 times a day. Oral administration is of particular interest.

The compounds of the invention will generally be administered in the form of a suitable pharmaceutical formulation. Thus, according to another aspect of the invention, there is provided a pharmaceutical formulation including preferably less than 50% by weight of a compound of the invention in admixture with a pharmaceutically acceptable adjuvant, diluent or carrier. The pharmaceutical formulation is preferably in unit dose form. Such forms include solid dosage forms, for example tablets, pills, capsules, powders, granules, and suppositories for oral, parenteral or rectal administration; and liquid dosage forms, for example sterile parenteral solutions or suspensions, suitably flavoured syrups, flavoured emulsions with edible oils such as cottonseed oil, sesame oil, coconut oil and peanut oil, and elixirs and similar pharmaceutical vehicles.

Solid formulations may be prepared by mixing the active ingredient with pharmaceutical carriers, for example conventional tabletting ingredients such as corn starch, lactose, sucrose, sorbitol, talc, stearic acid, magnesium stearate, dicalcium phosphate, gums and other diluents, for example water, to form a homogeneous preformulation formulation in which the active ingredient is uniformly dispersed so that it may be readily subdivided into equally effective unit dosage forms containing typically from 0.1 to about 500 mg of the active ingredient. The solid dosage forms may be coated or otherwise compounded to prolong the action of the formulation.

The formulations of the invention may also contain a human 5-α reductase inhibitory compound [see International Patent Application WO 95/28397], or a compound of the invention could be presented in a pharmaceutical pack also containing a human 5-α reductase inhibitory compound as a combined preparation for simultaneous, separate or sequential use.

The compounds of the invention may be tested in the screens set out below.

Contractile Responses of Human Prostate

Prostatic tissue was cut into longitudinal strips (approximately 3×2×10 mm) and suspended in organ baths under a resting tension of 1 g in Krebs Ringer bicarbonate of the following composition (mM): NaCl (119), KCl (4.7), $CaCl_2$ (2.5), $KH_2PO_4$ (1.2), $MgSO_4$ (1.2), $NaHCO_3$ (25), glucose (11), and gassed with 95% $O_2$/5% $CO_2$. The solution also contained 10 mM cocaine and 10 mM corticosterone. Tissues were exposed to a sensitising dose of (−)-noradrenaline (100 mM) and washed over a 45 minute period. Isometric contractions were obtained in response to cumulative additions of (−)-noradrenaline to obtain control curves in all tissues. A further curve was then generated in the presence or absence of antagonist (incubated for 2 hours). Antagonist affinity estimates ($pA_2$) were determined using a single concentration of competing antagonist, $pA_2$=−log [A]/(DR-1) where the dose ratio (DR), relative to corresponding controls, was produced by a single concentration of antagonist [A], assuming competitive antagonism and Schild regression close to unity.

Anaesthetised Dog Model of Prostatic Pressure and Blood Pressure

Mature male beagles (12–15 kg body weight) were anaesthetised with sodium pentobarbitone (30–50 mg/kg i.v.) and a tracheal cannula was inserted. Subsequent anaesthesia was maintained using pentobarbitone infusion. The animals were respirated with air using a Bird Mk8 respirator (Bird Corp., Palm Springs, Calif., USA) adjusted to maintain blood gasses in the range $pO_2$ 90–110 mm Hg, $pCO_2$ 35–45 mm Hg, pH 7.35–7.45. Body temperature was maintained at 36–37.5° C. using a heated operating table. Catheters were placed into the left femoral artery for recording blood pressure and into the left femoral vein for compound administration. Heart rate was recorded via the lead II E.C.G. A laparotomy was performed to cannulate both ureters to prevent change of fluid volume within the bladder. A 7F cardiac catheter (with a 1.5 ml capacity balloon tip) was inserted into the bladder via the urethra. The balloon was filled with air and the catheter withdrawn until the balloon became lodged in the prostate, which was confirmed by digital pressure. Balloon pressure was recorded via a Druck transducer. Prostatic pressure and haemodynamic parameters were made on a Grass Polygraph (Grass Instruments, Quincy, Mass., U.S.A.) and the data measured on line using a Motorola 68000-based microcomputer system (Motorola Inc., Temple, Ariz., U.S.A.). Compounds were made up in PEG 300 and administered i.v. through a catheter in the femoral vein. Responses to phenylephrine (1–16 μg/kg i.v. in saline) were obtained to generate control dose-response curves (two control curves for each experiment). Compounds were administered (in terms of compound base) at 10–300 μg/kg i.v. 5 min before construction of phenylephrine curves (constructed up to a maximum dose of 128 μg/kg in the presence of test compound).

Due to $α_1$-related dysrhythymic properties of phenylephrine, absolute maximal responses were not obtained but were taken as 10% greater than the control response obtained with 16 μg/kg phenylephrine. Drug concentrations were calculated on the basis of molar weight of compound/kg body weight thus allowing a "pseudo $pA_2$" calculation by Schild analysis using dose ratios derived from shifts in the phenylephrine dose-response curves.

The compounds of the invention may have the advantage that they are more potent, have a longer duration of action, have a broader range of activity, are more stable, have fewer side effects or are more selective (in particular they may have beneficial effects in benign prostatic hyperplasia without causing undesirable cardiovascular effects, for example because they are able to selectively antagonise prostatic receptor subtypes of the $α_1$-adrenoceptor), or have other more useful properties than the compounds of the prior art.

The invention is illustrated by the following examples, in which the following abbreviations may be used:

BuOH=butanol
DMA=dimethylacetamide
DMF=dimethylformamide
DMPU=1,3-dimethyl-3,4,5,6-tetrahydro-2(1H)-pyrimidone DMSO=dimethylsulphoxide
EDTA=ethylenediaminetetraacetic acid
EtOAc=ethyl acetate
EtOH=ethanol
h=hour
MeOH=methanol
min=minute
n-BuOH=n-butanol
p.s.i.=pounds per square inch
THF=tetrahydrofuran
tlc=thin layer chromatography Intermediate 1

1-(t-Butyloxycarbonyl)-1,4-diazepane

To a solution of homopiperazine (100 g, 1.0 mol) and triethylamine (210 ml, 152 g, 1.5 mol) in $CH_2Cl_2$ (500 ml) at 0° C. was added a solution of di-(t-butyl) dicarbonate (195 g, 0.89 mol) in $CH_2Cl_2$ (300 ml). The mixture was allowed to warm to room temperature and stirred for 18 h after which time the $CH_2Cl_2$ was evaporated under reduced pressure. The resulting residue was partitioned between ether and 2N citric acid and the aqueous layer was extracted with ether (4×200 ml). The aqueous layer was basified with 2N aqueous NaOH and then extracted with $CH_2Cl_2$ (4×400 ml). The combined $CH_2Cl_2$ extracts were washed with $H_2O$ (2×), saturated brine (1×) and dried over $MgSO_4$. Evaporation under reduced pressure followed by azeotroping with $CH_2Cl_2$ (4×) gave the title compound as a yellow waxy solid (94.3 g, 53%). $R_f$ 0.25 ($CH_2Cl_2$/MeOH/0.88$NH_3$ 90/10/1, v/v). MS m/z 201 ($MH^+$). Found: C,58.86; H,10.03; N,13.58; $C_{10}H_{20}N_2O_2$ 0.05.$CH_2Cl_2$ requires C, 59.02; H, 9.91; N,13.70%.

Intermediate 2

1-(t-Butyloxycarbonyl)-4-(4-morpholinecarbonyl)-1,4-diazepane

A solution of Intermediate 1 (92.0 g, 0.46 mol) and triethylamine (96.0 ml, 69.7 g, 0.69 mol) in $CH_2Cl_2$ (500 ml) at 0° C. was treated dropwise with a solution of 4-morpholinecarbonyl chloride (64.0 ml, 82.0 g, 0.55 mol) in $CH_2Cl_2$ (100 ml) and the reaction was stirred at room temperature under $N_2$ for 18 h. The reaction mixture was then diluted with $CH_2Cl_2$ (400 ml) and washed with 2N citric acid (3×400 ml), saturated brine (1×500 ml), dried over $MgSO_4$ and evaporated to give the title compound as an off-white solid (141.7 g, 98%). $R_f$ 0.80 ($CH_2Cl_2$/MeOH/ 0.88$NH_3$ 90/10/1, v/v). MS m/z 314 ($MH^+$). Found: C,57.50; H,8.69; N,13.41; $C_{15}H_{27}N_3O_4$ requires C, 57.50; H, 8.69; N,13.41%.

Intermediate 3

1-(4-Morpholinecarbonyl)-1,4-diazepane hydrochloride

A solution of Intermediate 2 (140.0 g, 0.44 mol) in $CH_2Cl_2$/MeOH (1/1, v/v, 600 ml) at 0° C. was saturated with HCl gas and the reaction mixture was stirred at room temperature under $N_2$ for 18 h after which time the reaction mixture was evaporated under reduced pressure and slurried in EtOAc to give, after filtration, a white hygroscopic solid. This was further purified by slurrying in acetone, filtering, washing with ether and drying in vacuo at 60° C. to give the title compound as a colourless solid (99.0 g, 90%). $R_f$ 0.41 ($CH_2Cl_2$/MeOH/0.88$NH_3$ 84/14/2, v/v). MS m/z 214 ($MH^+$). Found: C,47.50; H,8.10; N,16.55; $C_{10}H_{19}N_3O_2$ HCl 0.2.$H_2O$ requires C, 47.41; H, 8.12; N,16.59%.

Intermediate 4

1-Acetyl-4-(4-morpholinecarbonyl)-1,4-diazepane

To a solution of Intermediate 3 (50 g, 0.2 mol) and triethylamine (42 ml, 30.5 g, 0.3 mol) in $CH_2Cl_2$ (400 ml) at 5° C. was added acetic anhydride (23 ml, 24.9 g, 0.24 mol) dropwise over 15 min and the reaction was then stirred for a further 2 h at room temperature under $N_2$. Dilution with $CH_2Cl_2$ (600 ml) was followed by washing with saturated aqueous sodium bicarbonate (2×200 ml) and the combined aqueous layers extracted with $CH_2Cl_2$ (1×100 ml). The $CH_2Cl_2$ layers were combined and washed with saturated brine, dried over $MgSO_4$ and evaporated to give a light brown oil. This was dissolved in $CH_2Cl_2$ (300 ml) and treated with triethylamine (8 ml, 5.8 g, 0.06 mol) and EtOH (5 ml), stirred for 1 h at room temperature then washed with saturated aqueous sodium bicarbonate and the aqueous layer extracted with $CH_2Cl_2$ (5×). The combined $CH_2Cl_2$ layers were dried over $MgSO_4$ and evaporated under reduced pressure to give a yellow oil which was then azeotroped with $CH_2Cl_2$ (4×) to give the title compound as a yellow oil (47.1 g, 92%). $R_f$ 0.45 ($CH_2Cl_2$/MeOH/0.88 $NH_3$ 90/10/1, v/v). MS m/z 256 ($MH^+$). Found: C,52.62; H,8.18; N,15.02; $C_{12}H_{21}N_3O_3$ 0.3.$CH_2Cl_2$ requires C,52.61; H,7.75; N,14.96%.

EXAMPLE 1

4-Amino-6,7-dimethoxy-2-[4-(4-morpholinecarbonyl)-1,4-diazepan-1-yl]-5-(thiophen-3-yl)quinoline (a) 2-(3,4-Dimethoxyphenyl)-4,4-dimethyl-$\Delta^2$-oxazoline The subtitle compound was prepared from 3,4-dimethoxybenzoic acid according to the method of Meyers et al., J.Org.Chem., 39, 2787 (1974).

(b) 2-(3,4-Dimethoxy-2-iodophenyl)-4,4-dimethyl-$\Delta^2$-oxazoline nButyllithium (2.5M in hexane, 8.9 ml, 22.3 mmol) was added dropwise to a solution of the product of step (a) (4.2 g, 17.8 mmol) in dry ether (200 ml) at 0° C. and the reaction was stirred under $N_2$ for 2 h. This was followed by the dropwise addition of iodine (5.46 g, 21.5 mmol) in ether (100 ml) and the reaction was allowed to warm to room temperature over 1 h. The reaction mixture was poured onto $H_2O$, the ether layer was separated, washed with saturated aqueous sodium thiosulphate solution (1×) followed by saturated brine (1×) then dried over $MgSO_4$ and evaporated under reduced pressure to give the subtitle compound as a yellow oil (5.2 g, 80%). $R_f$ 0.60 ($CH_2Cl_2$/MeOH/0.88 $NH_3$ 90/10/1, v/v). MS m/z 362 ($MH^+$).

(c) 3,4-Dimethoxy-2-iodobenzonitrile

To a solution of the product of step (b) (5.2 g, 14.4 mmol) in pyridine (30 ml) was added phosphorus oxychloride (2.7 ml, 4.4 g, 28.8 mmol) and the reaction was heated to 85° C. for 18 h. The reaction mixture was cooled, partitioned between saturated aqueous sodium carbonate solution (300 ml) and then extracted with ether (2×100 ml). The ether layer was washed with 2N HCl (2×75 ml) followed by $H_2O$ (1×) and then dried over $MgSO_4$ and evaporated under reduced pressure to afford a yellow oil. This was purified by slurrying with hexane and filtering to give the subtitle compound as an off-white solid (2.82 g, 68%). $R_f$ 0.80 ($CH_2Cl_2$/MeOH 95/5, v/v). MS m/z 307 ($MH^+$). Found: C,38.03; H,2.88; N,4.64; $C_9H_8NO_2I$ 0.05. hexane requires C,38.05; H,2.97; N,4.77%.

(d) 3,4-Dimethoxy-2-iodo-6-nitrobenzonitrile

Nitronium tetrafluoroborate (1.73 g, 13.0 mmol) was added portionwise to a solution of the product of step (c) (2.67 g, 9.2 mmol) in acetonitrile (40 ml) at 0° C. The reaction was stirred for 30 min under $N_2$ and then poured into saturated aqueous sodium bicarbonate solution and extracted with EtOAc (1×). The organic layer was washed with saturated brine (1×), dried over $MgSO_4$ and evaporated under reduced pressure to give a residue which was slurried in hexane and filtered to give the subtitle compound as an off-white solid (2.51 g, 82%). $R_f$ 0.46 (EtOAc/hexane 1/1, v/v). MS m/z 352 ($MNH_4^+$).

(e) 6-Amino-3,4-dimethoxy-2-iodobenzonitrile

To a solution of the product of step (d) (3.50 g, 0.01 mol) in $CH_2Cl_2$ (90 ml) was added a solution of sodium dithionite (20.11, 0.11 mol) in $H_2O$ (60 ml). To the resulting mixture was added tetra-n-butylammonium chloride (1.45 g, 5.24 mmol) and the reaction was stirred vigorously for 1.5 h. The mixture was partitioned between $CH_2Cl_2$ and $H_2O$, the organic layer separated, dried over $MgSO_4$ and evaporated under reduced pressure. The residue was partitioned between EtOAc and 2N HCl and the aqueous layer was then basified with 2N aqueous NaOH and extracted with EtOAc (3×). The combined organic layers were dried over $MgSO_4$ and evaporated under reduced pressure to afford a residue which was purified on silica gel, eluting with $CH_2Cl_2$ to afford the subtitle compound as a colourless solid (1.69 g, 53%). $R_f$ 0.55 (EtOAc/hexane 1/1, v/v). MS m/z 322 ($MNH_4^+$).

(f) 3,4-Dimethoxy-2-iodo-6-{1-[4-(4-morpholinecarbonyl)-1,4-diazepan-1-yl]ethylideneamino}benzonitrile Phosphorus oxychloride (0.6 ml, 6.08 mmol) was added to a solution of Intermediate 4 (2.82 g, 11.0 mmol) in $CH_2Cl_2$ (20 ml) and the reaction was stirred for 20 min at room temperature. This was followed by the addition of the product of step (e) (1.68 g, 5.52 mmol) and the reaction was heated to reflux for 18 h after which time it was cooled, poured onto ice and the mixture basified with aqueous sodium bicarbonate and the product extracted with EtOAc (3×). The combined organic extracts were dried over $MgSO_4$ and evaporated under reduced pressure. The crude product was purified on silica gel, eluting with $CH_2Cl_2$/MeOH (97/3, v/v) to give the subtitle compound as a colourless solid (2.60 g, 87%). $R_f$ 0.15 ($CH_2Cl_2$). MS m/z 542 (MH+). Found: C,46.00; H,5.17; N,12.44; $C_{21}H_{28}N_5O_4I$ 0.1. $CH_2Cl_2$ requires C,46.08; H,5.17; N,12.74%.

(g) 4-Amino-6,7-dimethoxy-5-iodo-2-[4-(4-morpholinecarbonyl)-1,4-diazepan-1-yl]quinoline A solution of the product of step (f) (2.0 g, 3.7 mmol) in a mixture of THF (50 ml) and DMPU (10 ml) was cooled to −78° C. and treated with a solution of lithium diisopropylamide in cyclohexane (1.5M, 2.7 ml) under $N_2$. The reaction was warmed to 0° C. and stirred for 30 30 min after which time it was again cooled to −78° C. and a further portion of lithium diisopropylamide in THF (1.5M, 2.7 ml) was added. The reaction mixture was warmed to room temperature and stirred for 30 min, after which time it was again cooled to −78° C. and treated with a third portion of lithium diisopropylamide in THF (1.5M, 2.0 ml). The reaction was again warmed to room temperature and stirred for 20 min, after which time it was quenched with $H_2O$ and extracted with EtOAc (3×). The organic layer was washed sequentially with $H_2O$ and saturated brine, dried over $MgSO_4$ and evaporated under reduced pressure. The crude product was purified on silica gel, eluting with $CH_2Cl_2$/MeOH (98/2, v/v). The subtitle compound (1.30 g, 65%) was obtained as a light brown solid. $R_f$ 0.50 ($CH_2Cl_2$/MeOH/0.88$NH_3$ 90/10/1, v/v). MS m/z 542 (MH+). Found: C,45.71; H,5.26; N,12.44; $C_{21}H_{28}N_5O_4I$ 0.25.$CH_2Cl_2$ requires C,45.37; H,5.07; N,12.46%.

(h) 4-Amino-6,7-dimethoxy-2-[4-(4-morpholinecarbonyl)-1,4-diazepan-1-yl]-5-(thiophen-3-yl)quinoline To a solution of the product of step (g) (500 mg, 0.92 mmol) in a mixture of toluene (6 ml) and EtOH (3 ml) was added thiophene-3-boronic acid (236 mg, 1.85 mmol), tetrakis(triphenylphosphine)palladium (32 mg, 0.03 mmol) and 1M aqueous sodium carbonate solution (1 ml) and the reaction mixture was heated to reflux under $N_2$ for 18 h. On cooling, the reaction mixture was diluted with $H_2O$, extracted with EtOAc (3×), the combined organic layers dried over $MgSO_4$ and evaporated under reduced pressure. The product was purified on silica gel, eluting with $CH_2Cl_2$/MeOH/0.88$NH_3$ (90/10/1, v/v) to afford the title compound as a colourless foam (230 mg, 47%). $R_f$ 0.50 ($CH_2Cl_2$/MeOH/0.88$NH_3$ 90/10/1, v/v). MS m/z 498 (MH+). $^1$H NMR ($CDCl_3$) δ2.05 (2H, m), 3.13 (4H, m), 3.35 (2H, m), 3.50 (3H, s), 3.63 (6H, m), 3.71 (2H, m), 3.97 (5H, m), 4.30 (2H, bs), 5.76 (1H, s), 7.10 (2H, m), 7.45 (2H, m). Found: C,57.90; H,6.19; N,13.04. $C_{25}H_{31}N_5O_4S$ 0.3.$CH_2Cl_2$ requires C,57.85; H,6.07; N,13.32%.

EXAMPLE 2

4-Amino-6,7-dimethoxy-2-[4-(4-morpholinecarbonyl)-1,4-diazepan-1-yl]-5-(thiophen-2-yl)quinoline The title compound was prepared by the method of Example 1(h) from the compound of Example 1(g) and thiophene-2-boronic acid. The crude product was purified on silica gel, eluting with $CH_2Cl_2$/MeOH/0.88$NH_3$ (90/10/1, v/v) to afford the title compound (26%) as a colourless foam. MS m/z 498 (MH+). $^1$H NMR ($CDCl_3$) δ2.05 (2H, m), 3.13 (4H, m), 3.32 (2H, m), 3.61 (9H, m), 3.74 (2H, m), 3.97 (2H, m), 4.00 (3H, s), 4.60 (2H, bs), 5.77 (1H, s), 7.0–7.3 (1H, bs), 7.06 (1H, d), 7.15 (1H, dd), 7.52 (1H, d). Found: C,55.25; H,5.92; N,12.63. $C_{25}H_{31}N_5O_4S$ 0.7.$CH_2Cl_2$ requires C,55.40; H,5.86; N,12.57%;

EXAMPLE 3

4-Amino-6,7-dimethoxy-5-(2-fury)-2-[4-(4-morpholinecarbonyl)-1,4-diazepan-1-yl]quinoline The title compound was prepared by the method of Example 1(h) from the compound of Example 1(g) and furan-2-boronic acid [Florentin et al., J. Heterocyclic Chem., 13, 1265 (1976)]. The crude product was purified on silica gel, eluting with $CH_2Cl_2$/MeOH/0.88$NH_3$ (90/10/1, v/v) to afford the title compound (62%) as a colourless foam. $R_f$ 0.52 ($CH_2Cl_2$/MeOH/0.88$NH_3$ 90/10/1, v/v). MS m/z 482 (MH+). $^1$H NMR ($CDCl_3$) δ2.06 (2H, m), 3.16 (4H, m), 3.37 (2H, m), 3.50 (2H, m), 3.60 (7H, m), 3.71 (2H, m), 4.00 (5H, m), 5.80 (1H, s), 6.50 (1H, bs), 6.60 (1H, bs), 7.0–7.3 (1H, bs), 7.62 (1H, bs). Found: C,60.36; H,6.52; N,13.46. $C_{25}H_{31}N_5O_5$ 0.25.$CH_2Cl_2$ requires C,60.29; H,6.31; N,13.92%.

EXAMPLE 4

4-Amino-6,7-dimethoxy-5-(3-furyl)-2-[4-(4-morpholinecarbonyl)-1,4-diazepan-1-yl]quinoline The title compound was prepared by the method of Example 1(h) from the compound of Example 1(g) and furan-3-boronic acid [Florentin et al., J. Heterocyclic Chem., 13, 1265 (1976)]. The crude product was purified on silica gel, eluting with $CH_2Cl_2$/MeOH/0.88$NH_3$ (90/10/1, v/v) to afford the title compound (60%) as a colourless foam. MS m/z 482 (MH+). $^1$H NMR ($CDCl_3$) δ2.05 (2H, m), 3.13 (4H, m), 3.32 (2H, m), 3.55 (3H, s), 3.65 (6H, m), 3.74 (2H, m), 3.99 (5H, m), 4.55 (2H, bs), 5.77 (1H, s), 6.50 (1H,s), 7.1–7.4 (1H, bs), 7.50 (1H, s), 7.60 (1H, s). Found: C,60.22; H,6.38; N,13.76. $C_{25}H_{31}N_5O_5$ 0.25. $CH_2Cl_2$ requires C,60.29; H,6.31; N,13.92%.

EXAMPLE 5

4-Amino-6,7-dimethoxy-2-[4-(4-morpholinecarbonyl)-1,4-diazepan-1-yl]-5-(2-pyridyl)quinoline To a solution of the compound of Example 1(g) (700 mg, 1.29 mmol) in dioxane (15 ml) was added 2-(tri-n-butylstannyl)pyridine (1.42 g, 3.88 mmol), tetrakis (triphenylphosphine)-palladium (150 mg, 0.13 mmol), copper(I) iodide (37 mg, 0.19 mmol) and lithium chloride (271 mg, 6.5 mmol) and the mixture was heated to reflux under $N_2$ for 18 h. On cooling, the reaction mixture was concentrated under reduced pressure and the residue partitioned between 2N HCl and EtOAc. The aqueous layer was washed with three further portions of EtOAc and then basified with 2N aqueous NaOH. The product was then extracted with EtOAc (3×), dried over $MgSO_4$ and evaporated under reduced pressure. The crude product was purified on silica gel, eluting with $CH_2Cl_2/MeOH/0.88NH_3$ (90/10/1, v/v) to afford the title compound as a colourless solid (210 mg, 33%). $R_f$ 0.23 ($CH_2Cl_2/MeOH/0.88NH_3$ 90/10/1, v/v). MS m/z 493 (MH$^+$). $^1$H NMR (CDCl$_3$) δ2.05 (2H, m), 3.15 (4H, m), 3.32 (2H, m), 3.50 (2H, m), 3.55 (3H, s), 3.60 (2H, m), 3.68 (4H, m), 3.72 (2H, m), 3.94 (2H, m), 4.00 (3H, s), 5.80 (1H, s), 7.16 (1H, bs), 7.38 (1H, m), 7.48 (1H, m), 7.60 (1H,s), 8.74 (1H, bs). Found: C,60.89; H,6.41; N,16.03. $C_{26}H_{32}N_6O_4$ 0.3.$CH_2Cl_2$ requires C,60.71; H,6.32; N,16.14%.

EXAMPLE 6

4-Amino-6,7-dimethoxy-2-[4-(4-morpholinecarbonyl)-1,4-diazepan-1,4-yl]-5-(thiophen-3-yl)quinazoline (a) 3,4-Dimethoxy-2-iodobenzoic acid A solution of the compound of Example 1(b) (115 g, 0.32 mol) in a mixture of 3N HCl (530 ml) and EtOH (200 ml) was heated to reflux for 36 h. On cooling, the product was filtered, air dried and then washed with hexane. The solid was then dissolved in $CH_2Cl_2$, dried over $MgSO_4$ and evaporated under reduced pressure to afford the subtitle compound as a white solid. $R_f$ 0.38 (EtOAc). MS m/z 309 (MH$^+$).

(b) 3,4-Dimethoxy-2-iodobenzoic acid, ethyl ester

To a suspension of the product of step (a) (69.3 g, 0.23 mol) in $CH_2Cl_2$ at 0° C. was added oxalyl chloride (25 ml, 0.27 mol) and DMF (0.9 ml, 11.3 mmol) and the reaction was stirred or 18 h at room temperature. EtOH (20 ml, 0.34 mol) was then added to the reaction, which as stirred for a further 30 min, after which time it was treated with triethylamine (78 ml, 0.56 mol). The reaction mixture was partitioned between $CH_2Cl_2$ and $H_2O$, the organic layer separated, washed sequentially with 2N HCl (3×) and saturated brine, dried over $MgSO_4$ and evaporated under reduced pressure to give a brown oil. The product was purified on silica gel, eluting with $CH_2Cl_2$ to afford the subtitle compound as a brown oil (30 g, 39%). $R_f$ 0.73 (EtOAc). MS m/z 337 (MH$^+$).

(c) 3,4-Dimethoxy-2-iodo-6-nitrobenzoic acid, ethyl ester

Nitronium tetrafluoroborate (11 g, 84 mmol) was added to a solution of the product of step (b) (30 g, 64 mmol) in acetonitrile (300 ml) at 0° C. and the reaction was stirred for 1.5 h under $N_2$. The reaction mixture was then diluted with ether, basified with 2N aqueous NaOH and the aqueous layer extracted with ether (3×), the combined organic layers washed with saturated brine, dried over $MgSO_4$ and evaporated under reduced pressure. The product was purified on silica gel, eluting with hexane/EtOAc (85/15, v/v) to give the subtitle compound as a yellow solid (21.3 g, 87%). $R_f$ 0.77 (EtOAc). MS m/z 382 (MH$^+$).

(d) 6-Amino-3,4-dimethoxy-2-iodobenzoic acid, ethyl ester

The subtitle compound was prepared by the method of Example 1(e) from the product of step (c). The subtitle compound (84%) was obtained as a colourless solid. $R_f$ 0.67 (EtOAc). MS m/z 352 (MH$^+$).

(e) 2,4-Dihydroxy-6,7-dimethoxy-5-iodoquinazoline

Sodium cyanate (9 g, 0.14 mol) and trifluoroacetic acid (11 ml, 0.14 mol) were added to a stirred solution of the product of step (d) (12 g, 34.2 mmol) in $CH_2Cl_2$ and the stirring continued for 18 h. The reaction mixture was then evaporated under reduced pressure, $H_2O$ was added and the resulting solid filtered, washing with water. A suspension of the solid in $H_2O$ (50 ml) was treated with NaOH pellets (10 g) and the mixture heated to 60° C. for 30 min, after which time the reaction was cooled, neutralised with concentrated HCl and the resulting solid isolated by filtration, washing with $H_2O$ and ether. The subtitle compound was obtained as a colourless solid (8.4 g, 71%). $R_f$ 0.30 (EtOAc). $^1$H NMR (D$_6$-DMSO) δ: 3.70 (3H, s), 3.94 (3H, s), 9.13 (2H, bs), 12.10 (1H, bs).

(f) 2,4-Dihydroxy-6,7-dimethoxy-5-(thiophen-3-yl)quinazoline

The subtitle compound was prepared by the method of Example 1(h) from the product of step (e). The subtitle compound (84%) was obtained as a pale yellow solid. $R_f$ 0.28 (EtOAc). MS m/z 305 (MH$^+$).

(g) 4-Amino-2-chloro-6,7-dimethoxy-5-(thiophen-3-yl)quinazoline

The product of step (f) was added to a mixture of phosphorous oxychloride (9 ml, 96 mmol) and N,N-dimethylaniline (1 ml, 8 mmol) and the reaction mixture was heated to 110° C. for 5 h. On cooling, the reaction mixture was poured onto ice and partitioned between 2N HCl and ether. The organic layer was separated, washed with saturated brine and evaporated to give a brown oil. This was taken up into a mixture of $CH_2Cl_2$ (100 ml) and MeOH (100 ml), cooled to 0° C. and saturated with $NH_3$. The reaction was stirred for 20 h, saturated once more with $NH_3$ and stirred for a further 5 h. The reaction mixture was evaporated to dryness under reduced pressure and the residue partitioned between EtOAc and 2N HCl. The organic layer was washed with saturated brine, dried over $MgSO_4$ and evaporated under reduced pressure. Trituration with methanol and filtration afforded the subtitle compound as a colourless solid (255 mg, 25%). $R_f$ 0.78 (EtOAc). MS m/z 322 (MH$^+$).

(h) 4-Amino-6,7-dimethoxy-2-[4-(4-morpholinecarbonyl)-1,4-diazepan-1 -yl]-5-(thiophen-3-yl)quinazoline A mixture of the product of step (g) (220 mg, 0.68 mmol), triethylamine (0.24 ml, 1.7 mmol) and Intermediate 3 (250 mg, 1.0 mmol) in n-butanol (50 ml) was heated to 100° C. under $N_2$ for 5 days. After cooling, the reaction mixture was partitioned between 2N aqueous NaOH and EtOAc, the organic layer separated and washed with further portions of 2N aqueous NaOH (2×), followed by saturated brine (2×). After drying over $MgSO_4$ and evaporating under reduced pressure, the product was triturated with EtOAc, filtered and recrystallised from toluene to give the title compound as a colourless solid (33 mg, 10%). $R_f$ 0.08 (EtOAc). MS m/z 499 (MH$^+$). $^1$H NMR (CDCl$_3$) δ2.03 (2H, m), 3.18 (4H, m), 3.35 (2H, m), 3.50 (3H, s), 3.55 (2H, m), 3.65 (4H, m), 3.84 (2H, m), 3.99 (5H, m), 4.71 (2H, bs), 6.90 (1H, s), 7.12 (1H, d), 7.30 (1H, d), 7.50 (1H, dd). Found: C,57.86; H,6.03; N,16.45. $C_{24}H_{30}N_6O_4S$ requires C,57.82; H,6.07; N,16.85%.

EXAMPLE 7

4-Amino-6,7-dimethoxy-2-[4-(4-morpholinecarbonyl)-1,4-diazepan-1-yl]-5-(3-pyridyl)quinazoline (a) 4-Amino-6,7-dimethoxy-2-hydroxy-5-iodoquinazoline, sodium salt A suspension of the compound of Example 1(e) (9.16 g, 30 mmol) in $CH_2Cl_2$ (200 ml) was treated with sodium cyanate (7.9 g, 120 mmol) and trifluoroacetic acid (8.4 ml, 105 mmol) dropwise at room temperature under $N_2$ and the reaction stirred for 60 h. The mixture was then evaporated under reduced pressure and the resulting solid suspended in a mixture of aqueous NaOH (20 g in 150 ml) and MeOH (200 ml) and the reaction stirred at room temperature for 1 h. The resulting orange solution was then evaporated under reduced pressure to remove MeOH and the aqueous suspension formed was treated with EtOAc, filtered and the solid washed sequentially with $H_2O$ (3×), acetone (3×) and ether to afford the subtitle compound as a pale yellow solid (7.75 g, 69%). $R_f$ 0.53 ($CH_2Cl_2$/MeOH/0.88$NH_3$ 84/14/2, v/v). MS m/z 322 ($MH^+$).

(b) 4-Amino-2-chloro-6,7-dimethoxy-5-iodoquinazoline

DMF (1.8 ml, 23.0 mmol) was added dropwise to phosphorus oxychloride (5.4 ml, 57.6 mmol) and this was followed by addition of the product of step (a) (4.0 g, 11.5 mmol). The resulting mixture was heated to 90° C. for 30 min, after which time a further quantity (5 ml) of phosphorus oxychloride was added and heating continued for 18 h. The reaction mixture was cooled and carefully poured onto a mixture of EtOAc (400 ml) and $H_2O$ (200 ml), the mixture was neutralised with aqueous sodium bicarbonate and the aqueous layer extracted with EtOAc (2×), the combined organic layers combined, washed with saturated brine, dried over $MgSO_4$ and evaporated under reduced pressure to give a brown solid. This was suspended in 2N aqueous NaOH (300 ml), dioxane (100 ml) was added and the mixture heated to 90° C. with rapid stirring for 2 min. On cooling, a solid separated out and this was collected by filtration, washing sequentially with $H_2O$ and acetone and drying in vacuo at 60° C. to give the subtitle compound as an off-white solid (2.79 g, 66%). $R_f$ 0.76 (EtOAc). MS m/z 366, 368 ($MH^+$).

(c) 4-Amino-6,7-dimethoxy-5-iodo-2-[4-(4-morpholinecarbonyl)-1,4-diazepan-1-yl]quinazoline The subtitle compound was prepared by the method of Example 6(h) from the product of step (b). The subtitle compound was obtained in quantitative yield as a light brown foam. $R_f$ 0.41 (EtOAc). MS m/z 543 ($MH^+$).

(d) 4-Amino-6,7-dimethoxy-2-[4-(4-morpholinecarbonyl)-1,4-diazepan-1-yl]-5-(3-pyridyl)quinazoline To a solution of the product of step (c) (300 mg, 0.55 mmol) in a mixture of THF (25 ml) and $H_2O$ (5 ml) was added 3-pyridyldiethyl borane (485 mg, 3.3 mmol), tetrakis (triphenylphosphine)palladium (64 mg, 0.055 mmol) and potassium hydroxide (600 mg, 10.7 mmol) and the mixture was heated to reflux for 18 h under $N_2$. After cooling, the reaction mixture was partitioned between EtOAc and 2N aqueous NaOH, the aqueous layer separated and extracted with two further quantities of EtOAc. The combined organic layers were washed with saturated brine, dried over $MgSO_4$ and evaporated under reduced pressure to give a foam. The product was purified on silica gel, eluting with $CH_2Cl_2$/MeOH (95/5, v/v) to afford the title compound as a colourless foam (42 mg, 15%). $R_f$ 0.10 ($CH_2Cl_2$/MeOH 95/5, v/v). MS m/z 494 ($MH^+$). $^1$H NMR ($CDCl_3$) δ2.00 (2H, m), 3.18 (4H, m), 3.35 (2H, m), 3.50 (3H, s), 3.55 (2H, m), 3.67 (4H, m), 3.84 (2H, m) 3.97 (2H, m), 4.00 (3H, s), 4.48 (2H, bs), 6.97 (1H, s), 7.45 (1H, m), 7.74 (1H, m), 8.68 (1H, m), 8.74 (1H, m). Found: C,59.85; H,6.42; N,18.54. $C_{24}H_{31}N_7O_4$ 0.2.EtOAc 0.5.$H_2O$ requires C,59.57; H,6.51; N,18.85%.

EXAMPLE 8

4-Amino-6,7-dimethoxy-2-[4-(4-morpholinecarbonyl)-1,4-diazepan-1-yl]-5-(2-pyridyl)-quinazoline The title compound was prepared by the method of Example 5 from the compound of Example 7(c). The product was purified on silica gel eluting with $CH_2Cl_2$/MeOH (95/5, v/v) followed by trituration with hexane/EtOAc and recrystallisation from toluene to afford the title compound (19%) as a colourless solid. $R_f$ 0.25 ($CH_2Cl_2$/MeOH 95/5, v/v). MS m/z 494 ($MH^+$). $^1$H NMR ($CDCl_3$) δ: 2.00 (2H, p), 3.15 (4H, t), 3.30 (2H, dd), 3.45–3.58 (2H, m), 3.50 (3H, s), 3.65 (4H, t), 3.82 (2H, t), 3.94 (2H, t), 3.97 (3H, s), 4.55 (2H, s), 6.94 (1H, s), 7.39 (1H, m), 7.42 (1H, d), 7.82 (1H, t), 8.77 (1H, d). Found: C,59.91; H,6.27, N,19.23; $C_{25}H_{31}N_7O_4$ 0.5.$H_2O$ requires C,5 9.75; H,6.42, N,19.50%.

EXAMPLE 9

4-Amino-6,7-dimethoxy-5-(2-pyridyl)-2-(5,6,7,8-tetrahydro-1,6-naphthyrid-6-yl)quinazoline (a) 4-Amino-6,7-dimethoxy-5-iodo-2-(5,6,7,8-tetrahydro-1,6-naphthyrid-6-yl)quinazoline The subtitle compound was prepared by the method of Example 6(h) from the compound of Example 7(b) and 5,6,7,8-tetrahydro-1,6-naphthyridine [Shiozawa et al., Chem. Pharm. Bull., 32, 2522 (1984)]. The subtitle compound was obtained in quantitative yield as a brown foam. $R_f$ 0.35 ($CH_2Cl_2$/MeOH/0.88$NH_3$90/10/1, v/v). MS m/z 464 ($MH^+$).

(b) 4-Amino-6,7-dimethoxy-5-(2-pyridyl)-2-(5,6,7,8-tetrahydro-1,6-naphthyrid-6-yl)quinazoline The title compound was prepared by the method of Example 5 from the product of step (a). The product was purified on silica gel, eluting with $CH_2Cl_2$/MeOH (98/2, v/v) to afford the title compound (30%) as a pale yellow solid. $R_f$ 0.13 ($CH_2Cl_2$/MeOH 95/5, v/v). MS m/z 415 ($MH^+$). $^1$H NMR ($CDCl_3$) δ3.08 (2H, t), 3.52 (3H, s), 3.97 (3H, s), 4.20 (2H, t)4.67 (2H, bs), 5.00 (2H, s), 7.03 (1H, s), 7.12 (1H, m), 7.40 (1H, m), 7.48 (2H, m) 7.84 (1H, dt), 8.40 (1H, d), 8.78 (1H, d). Found: C,65.17; H,5.27, N,19.64; $C_{23}H_{22}N_6O_2$0.5.$H_2O$ requires C,65.24; H,5.48, N,19.84%.

EXAMPLE 10

4-Amino-6.7-dimethoxy-5-(2-pyrimidyl)-2-(5,6,7,8-tetrahydro-1,6-naphthyrid-6-yl)quinazoline The title compound was prepared by the method of Example 5 from the compound of Example 9(a) and 2-(tri-n-butylstannyl)pyrimidine [Sandosham et al., Tetrahedron, 50, 275 (1994)]. The product was purified on silica gel, eluting with $CH_2Cl_2$/MeOH (95/5, v/v) followed by partitioning between 2N HCl and EtOAc, washing the aqueous layer with EtOAc (3×), basifying with 2N aqueous NaOH and extracting with EtOAc (3×). The combined organic layers were dried over $MgSO_4$ and evaporated under reduced pressure to afford the title compound (21%) as a pale yellow solid. $R_f$ 0.39 ($CH_2Cl_2$/MeOH 9/1, v/v). MS m/z 416 ($MH^+$). $^1$H NMR ($CDCl_3$) δ: 3.06 (2H, t), 3.68 (3H, s), 3.98 (3H, s) 4.20 (2H, t), 4.61 (2H, bs), 5.00 (2H, s), 7.06 (1H, s), 7.13 (1H, m), 7.38 (1H, m), 7.50 (1H, d), 8.43 (1H, d), 8.92 (2H, d). Found: C,61.99; H,5.08, N,22.11; $C_{22}H_{21}N_7O_2$ 0.15.$CH_2Cl_2$0.1.EtOAc requires C,61.98; H,5.10, N,22.44%.

EXAMPLE 11

4-Amino-6,7-dimethoxy-5-(2-pyrimidyl)-2-(5,6,7,8-tetrahydro-1,3,6-triazanaphth-6-yl)quinazoline (a) 1-(t-Butyloxycarbonyl)-3-(N,N-dimethylaminomethylidene)-4-piperidone DMF dimethyl acetal (5.82 ml, 0.044 mol) was added to a stirred solution of 1-boc-4-piperidone [Ashwood et al., J. Chem. Soc., Perkin 1, 641 (1995)] (8.73 g, 0.044 mol) in DMF (80 ml) and the reaction mixture was heated to 80° C. under $N_2$ for 18 h. After cooling, the DMF was removed under reduced pressure and the residue was partitioned between EtOAc and $H_2O$, the organic layer washed with $H_2O$ and saturated brine, then dried over $MgSO_4$ and evaporated to afford the subtitle compound as a solid (8.44 g, 76%). $R_f$ 0.33 ($CH_2Cl_2$/MeOH/0.88$NH_3$ 90/10/1, v/v). MS m/z 255 ($MH^+$).

(b) 6-(t-Butyloxycarbonyl)-(5,6,7,8-tetrahydro-1,3,6-triazanaphthalene)

Sodium (762 mg, 0.033 mol) was added to EtOH (150 ml) followed by formamidine acetate (3.45 g, 0.033 mol) and the reaction was stirred at room temperature under $N_2$ for 30 min. A solution of the product of step (a) (8.43 g, 0.033 mol) in EtOH (50 ml) was then added and the reaction heated to reflux for 18 h after which time the mixture was cooled and concentrated under reduced pressure. The residue was partitioned between EtOAc and $H_2O$, the organic layer washed with saturated brine and dried over $MgSO_4$. Purification on silica gel, eluting with $CH_2Cl_2$/MeOH (96/4, v/v) afforded the subtitle compound as an oil (5.09 g, 65%). $R_f$ 0.57 ($CH_2Cl_2$/MeOH/0.88$NH_3$ 90/10/1, v/v). MS m/z 236 ($MH^+$).

(c) 5,6,7,8-Tetrahydro-1,3,6-triazanaphthalene hydrochloride

HCl was bubbled through a solution of the product of step (b) (4.80 g, 0.020 mol) in a mixture of MeOH and ether (50 ml, 1/1, v/v) at 0° C. until saturated. The mixture was then allowed to reach room temperature over 2 h, after which time a precipitate formed. This was isolated by decanting off the supernatant solution, washing with ether (2x) and drying in vacuo to afford the subtitle compound as a colourless solid (2.85 g, 81%). $R_f$ 0.13 ($CH_2Cl_2$/MeOH/0.88$NH_3$ 90/10/1, v/v). MS m/z 136 ($MH^+$).

(d) 4-Amino-6,7-dimethoxy-5-iodo-2-(5,6,7,8-tetrahydro-1,3,6-triazanaphth-6-yl)quinazoline The subtitle compound was prepared by the method of Example 6(h) from the product of step (b) and the compound of Example 7(b). The subtitle compound (65%) was obtained as a colourless solid. $R_f$ 0.52 ($CH_2Cl_2$/MeOH/ 0.88$NH_3$ 90/10/1, v/v). MS m/z 465 ($MH^+$).

(e) 4-Amino-6,7-dimethoxy-5-(2-pyrimidyl)-2-(5,6,7,8-tetrahydro-1,3,6-triazanaphth-6-yl)quinazoline The title compound was prepared by the method of Example 5 from the product of step (d) and 2-(tri-n-butylstannyl)pyrimidine. The product was purified on silica gel, eluting with $CH_2Cl_2$/MeOH (95/5, v/v) to afford the title compound (15%) as a colourless foam. $R_f$ 0.30 ($CH_2Cl_2$/ MeOH 9/1, v/v). MS m/z 417 ($MH^+$). $^1$H NMR ($CDCl_3$) δ: 3.03 (2H, t), 3.68 (3H, s), 4.00 (2H, m), 4.22 (2H, t), 4.47 (2H, bs), 5.00 (2H, s), 6.94 (1H, s), 7.07 (1H, s), 7.38 (1H, t), 8.55 (1H, s), 8.95 (2H, d), 9.00 (1H, s). Found: C,56.61; H,4.73, N,24.84; $C_{21}H_{20}N_8O_2$ 0.5.$CH_2Cl_2$ requires C,56.26; H,4.61, N,24.42%.

EXAMPLE 12

4-Amino-2-(7-aminosulfonyl-1,2,3,4-tetrahydroisoquinol-2-yl)-6,7-dimethoxy-5-(2-pyridyl)quinazoline (a) 4-Amino-2-chloro-6,7-dimethoxy-5-(2-pyridyl) quinazoline To a solution of the compound of Example 7(b) (1.0 g, 2.7 mmol) in dioxane (20 ml) was added 2-(tri-n-butylstannyl) pyridine (1.1 g, 3.0 mmol), lithium chloride (1.5 g, 35 mmol), tetrakis(triphenylphosphine)palladium (320 mg, 0.27 mmol) and copper(I) iodide (78 mg, 0.41 mmol) and the reaction was heated to 100° C. for 2 h. After cooling, the reaction mixture was partitioned between 2N HCl and EtOAc, the aqueous layer was extracted further with EtOAc (3x) then basified with 2N aqueous NaOH and extracted with EtOAc (3x). The combined organic layers were dried over $MgSO_4$ and evaporated under reduced pressure to give a pale yellow solid. This was suspended in ether and filtered to afford the subtitle compound as a colourless solid, (660 mg, 76%). $R_f$ 0.53 (EtOAc). MS m/z 317, 319 ($MH^+$).

(b) 4-Amino-2-(7-aminosulfonyl-1,2,3,3,4-tetrahydroisoquinol-2-yl)-6,7-dimethoxy-5-(2-pyridyl) quinazoline To a solution of the product of step (a) (250 mg, 0.8 mmol) in n-butanol/DMA (3:1, v/v, 8 ml) was added 1,2,3, 4-tetrahydroisoquinoline-7-sulfonamide hydrochloride (300 mg, 1.2 mmol) and triethylamine (0.33 ml, 2.4 mmol) and the reaction mixture heated to 100° C. under $N_2$ for 18 h. The reaction was then cooled, partitioned between EtOAc and 2N aqueous sodium hydroxide, the aqueous layer separated and extracted with EtOAc, the combined organic layer washed with $H_2O$, dried over $MgSO_4$ and evaporated under reduced pressure. Purification on silica gel, eluting with $CH_2Cl_2$/MeOH/0.88$NH_3$ (95/5/0.5, v/v) afforded an oil which was dissolved in $CH_2Cl_2$/MeOH and the product precipitated out with hexane to afford, on filtration and drying in vacuo, the title compound as a colourless solid (198 mg, 50%). $R_f$ 0.50 ($CH_2Cl_2$/MeOH/0.88$NH_3$ 84/14/2, v/v). MS m/z 493 ($MH^+$). $^1$H NMR ($D_6$-DMSO) δ: 0.90 (2H, m), 3.42 (3H, s), 3.94 (3H, s), 4.00 (2H, m), 4.94 (2H, s), 5.50 (2H, bs), 6.94 (1H, s), 7.26 (2H, s), 7.32 (1H, d), 7.40–7.55 (2H, m), 7.55–7.68 (2H, m), 7.94 (1H, t), 8.71 (1H, d). Found: C,58.57; H,5.35, N,15.75; $C_{24}H_{24}N_6O_4S$ 0.4.hexane 0.9.$H_2O$ requires C,58.97; H,5.73, N,15.64%.

EXAMPLE 13

4-Amino-6,7-dimethoxy-2-(2-isoindolinyl)-5-(2-pyridyl)quinazoline

The title compound was prepared by the method of Example 12(b) from the compound of Example 12(a) and isoindoline hydrochloride. The product was purified on silica gel, eluting with EtOAc followed by trituration with $CH_2Cl_2$ and ether to afford the title compound (51%) as a colourless foam. $R_f$ 0.42 (EtOAc). MS m/z 400 ($MH^+$). $^1$H NMR ($CDCl_3$) δ: 3.55 (3H, s), 4.03 (3H, s), 4.70 (2H, s), 4.97 (4H, s), 7.08 (1H, s), 7.21–7.50 (6H, m), 7.84 (1H, t), 8.88 (1H, d). Found: C,65.15; H,5.21, N,15.54; $C_{23}H_{21}N_5O_2$0.4.$CH_2Cl_2$ 0.25.ether requires C,64.83; H,5.42, N,15.50%.

EXAMPLE 14

4-Amino-6,7-dimethoxy-2-(2-pyridyl)-2-(5,6,7,8-tetrahydro-1,3,6-triazanaphth-6-yl)quinazoline The title compound was prepared by the method of Example 12(b) from the compound of Example 12(a) and the compound of Example 11(c). The product was purified on silica gel, eluting with EtOAc/MeOH (95/5, v/v) followed by trituration with ether to afford the title compound (35%) as a colourless solid. $R_f$ 0.18 ($CH_2Cl_2$/MeOH/0.88$NH_3$ 90/10/1, v/v). MS m/z 416 (MH$^+$). $^1$H NMR (CDCl$_3$) δ: 3.03 (2H, t), 3.52 (3H, s), 4.00 (3H, s), 4.20 (2H, t), 4.74 (2H, s), 5.00 (2H, s), 7.03 (1H, s), 7.40 (1H, m), 7.45 (1H, d), 7.84 (1H, t), 8.55 (1H, s), 8.78 (1H, d), 9.00 (1H, s). Found: C,60.94; H,5.13; N,21.93; $C_{22}H_{21}N_7O_2$0.3.$CH_2Cl_2$ requires C,60.74; H,4.94; N,22.24%.

EXAMPLE 15

4-Amino-6,7-dimethoxy-2-(7-methanesulfonamido-2,3,4,5-tetrahydro-1 H.3-benzazepin-3-yl)-5-(2-pyridyl)quinazoline (a) 3-t-Butyloxycarbonyl-7-nitro-2,3.4,5-tetrahydro-1H,3-benzazepine To a solution of 7-nitro-2,3,4,5-tetrahydro-1H,3-benzazepine [Pecherer et al., J. Heterocyclic Chem. 8, 779 (1971)] (1.92 g, 0.01 mol) in $CH_2Cl_2$ (40 ml) at 0° C. was added dropwise a solution of di-(t-butyl) dicarbonate in $CH_2Cl_2$ and the reaction allowed to stir at room temperature for 18 h. The reaction mixture was evaporated under reduced pressure to afford an oil which was taken up into $CH_2Cl_2$, washed with aqueous sodium carbonate solution (3×), 1N HCl (3×) and saturated brine (2×). The organic layer was separated, dried over $MgSO_4$ and evaporated to afford an oil. Trituration with hexane afforded the subtitle compound as a colourless solid (2.33 g, 80%). $R_f$ 0.8 ($CH_2Cl2$/MeOH 95/5, v/v). M.p. 106–108° C.

(b) 7-Amino-3-t-butyloxycarbonyl-2,3,4,5- tetrahydro-1 H,3 -benzazepine

A solution of the product of step (a) (2.1 g, 7.2 mmol) in a mixture of EtOAc (20 ml) and MeOH (20 ml) was hydrogenated over palladium on charcoal (5% w/w, 100 mg) at 345 kPa (50 p.s.i.) and room temperature for 3 h. After filtering, the filtrate was evaporated under reduced pressure to give the subtitle compound as an oil (2.0 g, quantitative). $R_f$ 0.7 ($CH_2Cl_2$/MeOH 9/1, v/v). Found: C,68.96; H,8.63; N,10.33; $C_{15}H_{22}N_2O_2$ require C,68.67; H,8.45; N,10.68%.

(c) 3-t-Butyloxycarbonyl-7-methanesulfonamido-2,3,4,5-tetrahydro-1H,3-benzazepine Methanesulfonyl chloride (0.56 ml, 7.3 mmol) was added dropwise to a solution of the product of step (b) (1.9 g, 7.2 mmol) in pyridine (40 ml) at 0° C. and the resulting orange solution was allowed to stir for 18 h. The reaction was evaporated under reduced pressure to give an oil which was dissolved in $CH_2Cl_2$ and extracted sequentially with aqueous sodium bicarbonate solution (3×) and saturated brine (3×). The organic layer was separated, dried over $MgSO_4$ and evaporated under reduced pressure to give an oil. The product was purified on silica gel, eluting with $CH_2Cl_2$/MeOH (95/5, v/v) followed by trituration with ether to give the subtitle compound as a white solid (1.2 g, 49%). $R_f$ 0.5 ($CH_2Cl_2$/MeOH 95/5, v/v). M.p. 153–154° C.

(d) 7-Methanesulfonamido-2,3,4,5-tetrahydro-1 H,3 -benzazepine hydrochloride

The subtitle compound was prepared from the product of step (d) by the method of Example 11(c). The subtitle compound (71%) was obtained as a colourless solid. $R_f$ 0.25 ($CH_2Cl_2$/MeOH/0.88$NH_3$ 84/14/2, v/v).

(e) 4-Amino-6,7-dimethoxy-2-(7-methanesulfonamido-2,3,4,5-tetrahydro-1H.3 -benzazepin-3-yl)-5-(2-pyridyl)quinazoline The title compound was prepared by the method of Example 12(b) from the product of step (d) and the compound of Example 12(a). The product was purified on silica gel, eluting with $CH_2Cl_2$/MeOH/0.88$NH_3$ (97/3/0.5, v/v) to give the title compound (40%) as a colourless solid. $R_f$ 0.31 (EtOAc/MeOH 95/5, v/v). MS m/z 521 (MH$^+$). $^1$H NMR (CDCl$_3$) δ: 2.90 (4H, bm), 3.00 (3H, s), 3.53 (3H, s), 4.00 (7H, bm), 4.65 (2H, bs), 6.68 (1H, bs), 6.96 (2H, s), 7.03 (1H, s), 7.10 (1H, m), 7.42 (1H, m), 7.48 (1H, m), 7.95 (1H, t), 8.80 (1H, d). Found: C,56.65; H,5.26; N,14.66; $C_{26}H_{28}N_6O_4S$ 0.5.$CH_2Cl_2$ requires C,56.53; H,5.19; N,14.93%.

EXAMPLE 16

4-Amino-6,7-dimethoxy-2-[7-(4-morpholinesulfonamido)-1,2,3,4-tetrahydroisoquinolin-2-yl]-5-(2-pyridyl)quinazoline (a) 7-(4-Morpholinesulfonamido)-1,2,3,4-etrahydroisoquinoline To a solution of 2-trifluoroacetyl-1,2,3,4-tetrahydroisoquinoline-7-sulfonyl chloride [Blank et al J. Med. Chem. 23, 837 (1980)] (1.0 g, 3.3 mmol) in THF (40 ml) was added morpholine (0.74 ml, 8.5 mmol) and a thick white precipitate was formed immediately. After 5 min a solution of sodium carbonate (1.7 g, 16.5 mmol) in $H_2O$ (20 ml) was added followed by a mixture of MeOH and $H_2O$ (20 ml, 1/1, v/v). The resulting clear solution was stirred for 18 h at room temperature after which time the reaction was partitioned between EtOAc and 2N aqueous NaOH and the aqueous layer was separated and extracted with EtOAc (8×). The combined organic layers were washed with brine, dried over $MgSO_4$ and evaporated to give the subtitle compound as a colourless solid (650 mg, 70%). $R_f$ 0.50 ($CH_2Cl_2$/MeOH/0.88$NH_3$ 90/10/1, v/v). MS m/z 283 (MH$^+$).

(b) 4-Amino-6,7-dimethoxy-2-[7-(4-morpholinesulfonamido)-1,2,3,4-tetrahydro-isoquinolin-2-yl]-5-(2-pyridyl)quinazoline The title compound (40%) was prepared by the method of Example 12(b) from the product of step (a) and the compound of Example 12(a). MS m/z 563 (MH$^{m+}$). $^1$H NMR (CDCl$_3$). $^1$H NMR (CDCl$_3$) δ: 3.00 (6H, m), 3.53 (3H, s), 3.73 (4H, m), 3.98 (3H, s), 4.12 (2H, t), 4.70 (2H, bs) 5.70 (2H, s), 7.05 (1H, s), 7.32 (1H, d), 7.40 (1H, m), 7.48 (1H, d), 7.53 (1H, d), 7.06 (1H, s), 7.84 (1H, t), 8.78 (11H, d).

EXAMPLE 17

4-Amino-6,7-dimethoxy-2-(2-methyl-5,6,7,8-tetrahydro-1,3,6-triazanaphth-6-yl)-5-(2-pyridyl)quinazoline (a) 6-(t-Butyloxycarbonyl)-2-methyl-(5,6,7,8-tetrahydro-1,3,6-triazanaphthalene A solution of sodium ethoxide in EtOH was prepared by the addition of sodium (690 mg, 30.0 mmol) to EtOH (75 ml) and was treated with the compound of Example 11(a) (7.62 g, 30.0 mmol) and acetamide hydrochloride (3.12 g, 33.0 mmol). The reaction was heated to reflux for 18 h, after which time it was partitioned between EtOAc and aqueous sodium bicarbonate, the organic layer was separated and dried over $MgSO_4$ and evaporated under reduced pressure to afford an oil. The product was purified on silica gel, eluting with EtOAc/MeOH (98/2, v/v) to afford the subtitle compound as a crystalline solid (6.47 g, 87%). $R_f$ 0.31 (EtOAc/MeOH 95/5, v/v). $^1$H NMR (CDCl$_3$) δ: 1.48 (9H, s), 2.68 (3H, s), 2.92 (2H, m), 3.73 (2H, m), 4.57 (2H, s), 8.38 (1H, s)

(b) 2-Methyl-5,6,7,8-tetrahydro-1,3,6-triazanaphthalene hydrochloride

The subtitle compound was prepared by the method of Example 11(c) from the product of step (a). The product was partitioned between EtOAc and 2N aqueous NaOH and the aqueous layer extracted repeatedly with EtOAc. The combined organic layers were dried over $MgSO_4$ and evaporated under reduced pressure to afford the subtitle compound (7%) as a yellow oil that crystallised on standing. $^1H$ NMR $(CDCl_3)$ δ: 2.70 (3H, s), 2.90 (2H, t), 3.25 (2H, t), 4.00 (2H, s), 8.38 (1H, s).

(c) 4-Amino-6,7-dimethoxy-2-(2-methyl-5,6,7,8-tetrahydro-1,3,6-triazanaphth-6-yl)-5-(2-pyridyl)quinazoline The title compound was prepared by the method of Example 12(b) from the product of step (b) and the compound of Example 12(a). The product was purified on silica gel, eluting with $CH_2Cl_2$/MeOH (94/6, v/v) to afford the title compound (32%) as a colourless foam. $R_f$ 0.33 ($CH_2Cl_2$/ $MeOH/0.88NH_3$ 90/10/1, v/v). MS m/z 430 (MH$^+$). $^1H$ NMR $(CDCl_3)$ δ: 2.65 (3H, s), 2.97 (2H, m), 3.50 (3H, s), 3.98 (3H, s), 4.15 (2H, t), 4.73 (2H, bs), 4.93 (2H, bs), 7.00 (1H, s), 7.40 (2H, m), 7.82 (1H, t), 8.42 (1H, s), 8.75 (1H, d). Found: C,56.65; H,5.26; N,14.66; $C_{23}H_{23}N_7O_2$ 0.3.$CH_2Cl_2$ requires C,56.53; H,5.19; N,14.93%.

EXAMPLE 18

4-Amino-6,7-dimethoxy-5-(2-pyridyl)-2-(5,6,7,8-tetrahydro-1,3,7-triazanaphth-7-yl)-quinazoline (a) 1-Trityl-3-piperidone Trityl chloride (13.1 g, 47.0 mmol) was added to a stirred suspension of 3-piperidone hydrochloride (5.79 g, 42.7 mmol) and triethylamine (14.9 ml, 107 mmol) in $CH_2Cl_2$ (100 ml) and the reaction was stirred for 16 h under $N_2$ at room temperature. The resulting mixture was filtered and the filtrate washed sequentially with $H_2O$ and 5% aqueous citric acid, dried over $MgSO_4$ and evaporated under reduced pressure. Trituration with pentane afforded the subtitle compound as a colourless solid (4.8 g, 33%). $R_f$ 0.23 ($CH_2Cl_2$/ pentane 2/3, v/v). $^1H$ NMR $(CDCl_3)$ δ: 2.05 (2H, m), 2.35 (2H, m), 2.45 (2H, m), 2.85 (2H,s), 706–755 (15H, m).

(b) 4-(N,N-Dimethylaminomethylidene)-1-trityl-3-pipieridone

The subtitle compound was prepared by the method of Example 11(a) from the product of step (a). Crystallisation from ether afforded the subtitle compound (52%) as a colourless solid. $R_f$ 0.23 ($CH_2Cl_2$/pentane 2/3, v/v). $^1H$ NMR $(CDCl_3)$ δ: 2.35 (2H, t), 2.87 (2H, t), 2.97 (2H, s), 3.13 (6H, s), 7.13 (3H, m), 7.24 (7H, m), 7.50 (6H, m).

(c) 7-Trityl-5,6,7,8-tetrahydro-1,3,7-triazanaphthalene

The subtitle compound was prepared by the method of Example 11(b) from the product of step (b). The product was purified by chromatography on silica gel, eluting with $CH_2Cl_2$/ether (9/1, v/v) to afford the subtitle compound (51%). $R_f$ 0.33 ($CH_2Cl_2$/ether 85/15, v/v). $^1H$ NMR $(CDCl_3)$ δ: 2.60 (2H, t), 2.97 (2H, t), 3.58 (2H, s), 7.06–7.37 (8H, t), 7.52 (7H, m), 8.45 (1H, s), 8.90 (1H, s).

(d) 5,6,7,8-Tetrahydro-1,3,7-triazanaphthalene hydrochloride

The subtitle compound was prepared by the method of Example 11(c) from the product of step (c). The product crystallised from MeOH/ether to afford the subtitle compound (65%) as an orange hygroscopic solid. $^1H$ NMR ($d_6$-DMSO) δ: 3.06 (2H, m), 3.40 (2H, m), 4.26 (2H, s), 8.68 (1H, s), 9.00 (1H, s), 9.96 (2H, bs).

e) 4-Amino-6,7-dimethoxy-5-(2-pyridyl)-2-(5,6,8-tetrahydro-1,3,7-triazanaphth-7-yl)-quinazoline The title compound was prepared by the method of Example 12(b) from the product of step (d) and the compound of Example 12(a). The product was purified on silica gel, eluting with $CH_2Cl_2$/MeOH (95/5, v/v) to give the title compound (66%) as a light brown solid. $R_f$ 0.20 ($CH_2Cl_2$/MeOH 95/5, v/v). MS m/z 416 (MH$^+$). $^1H$ NMR $(CDCl_3)$ δ: 2.92 (2H, t), 3.52 (3H, s), 4.00 (3H, s), 4.18 (2H, t), 4.70 (2H, bs), 5.18 (2H, bs), 7.05 (1 H, s), 7.41 (1H, m), 7.43 (1H, m), 7.83 (1H, t), 8.50 (1H, s), 8.79 (1H, d), 9.02 (1H, s). Found: C,61.24; H,4.91; N,22.35; $C_{22}H_{21}N_7O_2$ 0.25.$CH_2Cl_2$ requires C,61.20; H,4.96; N,22.46%.

EXAMPLE 19

4-Amino-6,7-dimethoxy-2-(5-methanesulfonamido-1,2,3,4-tetrahydroisoquinol-2-yl)-5-(2-pyridyl)quinazoline (a) 5-Methanesulfonamidoisoquinoline Methanesulfonyl chloride (3.2 ml, 42 mmol) was added to a solution of 5-aminoisoquinoline (5.0 g, 35 mmol) in pyridine (40 ml) and the mixture was allowed to stand for 72 h. The reaction mixture was then poured into aqueous citric acid (10%, 400 ml) and extracted with EtOAc (2×230 ml). The organic layer was evaporated to give a residue which was purified on silica gel, eluting with $CH_2C_2$/MeOH to afford the subtitle compound as a solid (3.55 g, 46%). $R_f$ 0.03 ($CH_2Cl_2$/ether 4/1, v/v). $^1H$ NMR ($D_6$-DMSO) δ: 3.07 (3H, s), 7.68 (1H, t), 7.75 (1H, d), 8.03 (1H, d), 8.10 (1H, d), 8.54 (1H, d), 9.32 (1H, s), 9.79 (1H, bs).

(b) 5-Methanesulfonamido-1,2,3,4-tetrahydroisoquinoline hydrochloride mA solution of the product of step (a) (3.50 g, 15.7 mmol) in EtOH (205 ml) was treated with platinum dioxide (1.5 g) and 1N HCl (15.7 ml). The mixture was hydrogenated at 414 kPa (60 p.s.i.) for 16 h, after which time the reaction was filtered. The filtrate was evaporated under reduced pressure and triturated with $CH_2Cl_2$ to afford the subtitle compound as a colourless solid. The solid residue from the filtration was taken up into $MeOH/H_2O$ (1/2, v/v), the suspension filtered, washed with $CH_2Cl_2$ (3×) and the filtrate evaporated to afford a second crop of the subtitle compound (total yield 3.45 g, 84%). $R_f$ 0.21 ($CH_2Cl_2$/MeOH/0.88$NH_3$ 90/10/1, v/v). $^1H$ NMR ($d_6$-DMSO) δ: 2.96–3.10 (2H, m), 3.31 (3H, m), 4.21 (2H, s), 7.12 (1H, m), 7.26 (2H, m), 9.24 (1H, s), 9.61 (2H, bs)

(c) 4-Amino-6,7-dimethoxy-2-(5-methanesulfonamido-1,2,3,4-tetrahydroisoquinol-2-yl)-5-(2-pyridyl)quinazoline The title compound was prepared by the method of Example 12(b) from the product of step (b) and the compound of Example 12(a). The product was purified on silica gel, eluting with $CH_2Cl_2$/MeOH (95/5, v/v) to give the title compound (80%) as a light brown solid. $R_f$ 0.21 ($CH_2Cl_2$/MeOH 95/5, v/v). MS m/z 507 (MH$^+$). $^1H$ NMR $(CDCl_3)$ δ: 2.80 (2H, t), 3.02 (2H, s), 3.53 (3H, s), 4.00 (3H, s), 4.12 (2H, t), 4.67 (2H, bs), 4.97 (2H, s), 6.15 (1H, s), 7.03 (1H, s), 7.10 (1H, d), 7.21 (1H, d), 7.32 (1H, d), 7.42 (1H, m), 7.46 (1H, d), 7.48 (1H, t), 8.79 (1H, d). Found: C,55.09; H,4.90; N,14.94 $C_{25}H_{26}N_6O_4S$ 0.56.$CH_2Cl_2$ requires C,55.38; H,4.93; N,15.16%.

EXAMPLE 20

4-Amino-6,7-dimethoxy-2-[7-(1-piperazinesulfonyl)-1,2,3,4-tetrahydroisoquinolin-2-yl]-5-(2-pyridyl)quinazoline (a) 7-(4-t-Butyloxycarbonyl-1-piperazinesulfonyl)-1,2,3,4-tetrahydroisoquinoline The subtitle compound was prepared by the method of Example 16(a) from 1-t-butyloxycarbonylpiperazine and 2-trifluoroacetyl-1,2,3,4-tetrahydroisoquinoline-7-sulfonyl chloride. The product was purified on silica gel, eluting with $CH_2Cl_2$/MeOH (93/7, v/v) to afford the subtitle compound (35%) as a colourless solid. $R_f$ 0.56 ($CH_2Cl_2$/MeOH 9/1, v/v). MS m/z 382 (MH$^+$).

(b) 4-Amino-6,7-dimethoxy-2-[7-(4-t-butyloxycarbonyl-1-piperazinesulfonyl)-1,2,3,4-tetrahydroisoquinolin-2-yl]-5-(2-pyridyl)quinazoline The subtitle compound was prepared by the method of Example 12(b) from the product of step (a) and the compound of Example 12(a). The product was purified on silica gel, eluting with $CH_2Cl_2$/MeOH (96/4, v/v) to give the subtitle compound (69%) as a colourless solid. $R_f$ 0.25 ($CH_2Cl_2$/MeOH 96/4, v/v).

(c) 4-Amino-6,7-dimethoxy-2-[7-(1-piperazinesulfonyl)-1 2,3 4-tetrahydroisoquinolin-2-yl]-5-(2-pyridyl)quinazoline trihydrochloride The title compound was prepared by the method of Example 11(c). The product was triturated with $CH_2Cl_2$ to give the title compound (58%) as a colourless solid. MS m/z 562 (MH$^+$). $^1$H NMR (d$_6$-DMSO) δ: 3.03–3.25 (11H, m), 3.50 (3H, s), 4.00 (3H, s), 4.12 (2H, t), 5.17 (2H, bs), 5.58 (1H, bs), 7.52–7.68 (5H, m), 7.94 (1H, s), 8.07 (1H, t), 8.62 (1H, bs), 8.80 (1H, d), 9.20 (2H, bs), 12.72 (1H, bs). Found: C,46.88; H,5.61; N,13.68; $C_{28}H_{31}N_7O_4S$ 3.HCl 2.5.$H_2O$ requires C,46.96; H,5.48; N,13.69%.

EXAMPLE 21

4-Amino-2-[5-(N,N-diethylaminomethyl)-1,2,3,4-tetrahydroisoquinolin-2-yl]-6,7-dimethoxy-5-(2-pyridyl)quinazoline (a) 5-(Trifluoromethanesulfonato)isoquinoline Pyridine (8.35 ml, 0.10 mol) was added to a solution of 5-hydroxyisoquinoline (5.0 g, 0.034 mol) in $CH_2Cl_2$, the solution was cooled to −40° C. and triflic anhydride (8.47 ml, 0.052 mol) was added dropwise. The reaction was allowed to reach room temperature and stirred for 18 h, after which time $H_2O$ was added, the organic layer was separated, washed with saturated brine, dried over $MgSO_4$ and evaporated under reduced pressure. The product was purified on silica gel, eluting with $CH_2Cl_2$/MeOH (98/2, v/v) to give the subtitle compound as a solid (6.93 g, 73%). $R_f$ 0.70 ($CH_2Cl_2$/MeOH 9/1, v/v).

(b) 5-(N,N-Diethylcarboxamido)isoquinoline

To a solution of the product of step (a) (500 mg, 1.8 mmol) in DMF (4 ml) was added palladium acetate (12 mg, 0.054 mmol), triphenylphosphine (28 mg, 0.11 mmol) and diethylamine (3.7 ml, 36 mmol) and the reaction was heated at 60° C. under a balloon of CO for 20 h. After cooling, the reaction mixture was diluted with saturated brine and extracted with EtOAc (3×), the combined organic extracts were dried over $MgSO_4$ and evaporated under reduced pressure. The product was purified on silica gel, eluting with $CH_2Cl_2$/MeOH (97/3, v/v) to give the subtitle compound as a solid (220 mg, 53%). $R_f$ 0.45 ($CH_2Cl_2$/MeOH 9/1, v/v). MS m/z 229 (MH$^+$).

(c) 5-(N,N-Diethylcarboxamido)-1,2,3,4-tetrahydroisoquinoline

The subtitle compound was prepared by the method of Example 19(b) from the product of step (b). The crude product was partitioned between $CH_2Cl_2$ and aqueous sodium bicarbonate solution and the aqueous layer was extracted with further portions of $CH_2Cl_2$. The combined organic extracts were dried over $MgSO_4$ and evaporated under reduced pressure. The product was purified on silica gel, eluting with $CH_2Cl_2$/MeOH/0.88$NH_3$ (90/10/1, v/v) to give the subtitle compound (66%) as an oil. $R_f$ 0.09 ($CH_2Cl_2$/MeOH/0.88$NH_3$ 90/10/1, v/v). MS m/z 233 (MH$^+$).

(d) 5-(N,N-Diethylaminomethyl)-1,2,3,4-tetrahydroisoquinoline

A solution of borane in THF (1M, 18 ml, 18.0 mmol) was added dropwise to a solution of the product of step (c) (1.39 g, 6.0 mmol) in THF (20 ml). The reaction mixture was heated to reflux for 18 h under $N_2$ after which time the reaction mixture was cooled, added to a mixture of 2N HCl/MeOH (1/1, v/v, 100 ml) and stirred for 2 h. The MeOH was removed under reduced pressure, the reaction mixture was basified to pH 10 and extracted with $CH_2Cl_2$ (3×). The combined organic layers were dried over $MgSO_4$ and evaporated under reduced pressure to give the subtitle compound as an oil (840 mg, 64%). MS m/z 219 (MH$^+$). $^1$H NMR (CDCl$_3$) δ: 1.05 (6H, t), 2.40 (1H, bs), 2.52 (4H, q), 2.89 (2H, t),3.20 (2H, t), 3.47 (2H, s), 4.06 (2H, s), 6.90 (1H, d), 7.09 (1H, t), 7.20 (1H, d)

(e) 4-Amino-2-[5-(N,N-diethylaminomethyl)-1,2,3,4-tetrahydroisoquinolin-2-yl]-6,7-dimethoxy-5-(2-pyridyl)quinazoline The title compound was prepared by the method of Example 12(b) from the product of step (d) and the compound of Example 12(a). The product was purified on silica gel, eluting with $CH_2Cl_2$/MeOH/0.88$NH_3$ (90/10/1, v/v) to give the title compound (30%) as a colourless foam. MS m/z 499 (MH$^+$). $^1$H NMR (CDCl$_3$) δ: 1.05 (6H, t), 2.53 (4H, q), 3.00 (2H, t), 3.50 (3H, s), 3.53 (2H, s), 4.00 (3H, s), 4.08 (2H, t), 4.73 (2H, bs), 4.98 (2H, s), 7.0–7.3 (4H, m), 7.40 (2H, m), 7.82 (1H, t), 8.77 (1H, d). Found: C,68.36; H, 6.71; N,15.96; $C_{29}H_{34}N_6O_2$ 0.2.$CH_2Cl_2$ requires C,68.01; H,6.72; N,16.30%.

EXAMPLE 22

4-Amino-6,7-dimethoxy-2-(5-methanesulfonamido-1,2,3,4-tetrahydroisoquinol-2-yl)-5-(2-pyrimidyl)quinoline (a) 2-Acetyl-(5-methanesulfonamido)-1,2,3,4-tetrahydroisoquinoline To a solution of the compound of Example 19(b) (2.87 g, 10.9 mmol) in $CH_2Cl_2$ at 0° C. was added acetic anhydride (1.2 ml, 13.1 mmol) and triethylamine (3.4 ml, 24.0 mmol) and the reaction was stirred at room temperature for 16 h after which time the reaction mixture was partitioned between EtOAc and aqueous sodium bicarbonate solution and the aqueous phase extracted with further portions of EtOAc. The combined organic extracts were dried over $MgSO_4$ and evaporated to afford an oil. This was dissolved in MeOH (15 ml) and treated with aqueous sodium carbonate solution (7%, w/w, 15 ml) and the mixture stirred for 16 h at room temperature, after which time the MeOH was removed under reduced pressure, the pH was adjusted to pH 8 with 2N aqueous HCl and the product was extracted with EtOAc (2×). The combined organic extracts were dried over $MgSO_4$ and evaporated to give an oil which was purified on silica gel, eluting with $CH_2Cl_2$/MeOH (95/5, v/v) to give the product as an oil (2.0 g, 68%). $R_f$ 0.20 ($CH_2Cl_2$/MeOH 9/5, v/v). MS m/z 269 (MH$^+$).

(b) 3,4-Dimethoxy-2-iodo-6-[1-(5-methanesulfonamido-1,2,3,4-tetrahydroisoquinol-2-yl)ethylideneamino] benzonitrile The subtitle compound was prepared by the method of Example 1(f) from the product of step (a) and the compound of Example 1(e). The product was purified on silica gel, eluting with $CH_2Cl_2$/MeOH (98/2, v/v) to afford the subtitle compound (93%) as a colourless foam. $R_f$ 0.30 ($CH_2Cl_2$/MeOH 95/5, v/v). MS m/z 555 (MH$^+$).

(c) 3,4-Dimethoxy-6-[1-(5-methanesulfonamido-1.2.3,4-tetrahydroisoquinol-2-yl)ethylideneamino]-2-(2-pyrimidyl) benzonitrile The subtitle compound was prepared by the method of Example 5 from the product of step (b) and 2-(tri-n- butylstannyl)pyrimidine. The product was purified on silica gel, eluting with $CH_2Cl_2$/MeOH (96/4, v/v) to give the subtitle compound (32%) as a foam. $R_f$ 0.11 ($CH_2Cl_2$/MeOH 95/5, v/v). MS m/z 507 (MH+).

(d) 4-Amino-6,7-dimethoxy-2-(5-methanesulfonamido-1,2,3,4-tetrahydroisoquinol-2-yl)-5-(2-pyrimidyl)quinoline A solution of zinc chloride in THF (0.5M, 10,6 ml, 5.3 mmol) was added to a solution of the product of step (c) (180 mg, 0.36 mmol) in THF (5 ml) and the reaction mixture was heated to reflux for 70 h, after which time a further portion of zinc chloride in THF (0.5M, 3.5 ml) was added and heating continued at reflux for a further 7 h. After cooling, the reaction mixture was partitioned between $CH_2Cl_2$ and a solution of EDTA in 2N aqueous NaOH, the organic layer was washed with saturated brine and dried over $MgSO_4$. The product was purified on silica gel, eluting with $CH_2Cl_2$/MeOH/0.88$NH_3$ (90/10/1, v/v) to afford the title compound as a colourless solid (38 mg, 21%). $R_f$ 0.28 ($CH_2Cl_2$/MeOH/0.88$NH_3$ 90/10/1, v/v). MS m/z 507 (MH+). $^1$H NMR ($CDCl_3$) δ: 2.83 (2H, m), 3.00 (3H, s), 3.64 (3H, s), 3.96 (5H, m), 4.46 (2H, bs), 4.77 (2H, s), 6.07 (1H, s), 7.0–7.2 (1H, bs), 7.15 (1H, t), 7.22 (1H, d), 7.43 (1H, t), 7.50 (1H, bs), 8.96 (2H, d).

EXAMPLE 23

4-Amino-6-ethoxy-2-(5-methanesulfonamido-1,2,3,4-tetrahydroisoquinol-2-yl)-7-methoxy-5-(2-pyridyl)quinoline (a) 3-Hydroxy-2-iodo-4-methoxy-6-nitrobenzonitrile To a solution of the compound of Example 1(d) (10.0 g, 30 mmol) in collidine (100 ml) was added lithium iodide (4.0 g, 30 mmol) and the reaction was stirred at room temperature for 18 h followed by heating at 100° C. for 1.5 h. After cooling, the reaction mixture was partitioned between 2N aqueous NaOH and EtOAc, the layers were separated and the product was extracted with 3 further EtOAc washes. The combined organic layers were washed with 2N HCl (2×), dried over $MgSO_4$ and evaporated under reduced pressure. The crude product was purified on silica gel, eluting with $CH_2Cl_2$/MeOH (97/3, v/v) to afford the subtitle compound as a colourless solid (6.96 g, 73%). $R_f$ 0.16 ($CH_2Cl_2$/MeOH 95/5, v/v). MS m/z 338 ($MNH_4^+$).

(b) 3-Ethoxy-2-iodo-4-methoxy-6-nitrobenzonitrile

To a solution of the product of step (a) (6.95 g, 21.7 mmol) and bromoethane (1.78 ml, 23.8 mmol) in DMF (70 ml) was added potassium carbonate (4.49 g, 32.5 mmol) and the reaction was heated to 60° C. for 18 h. After cooling, the reaction mixture was partitioned between 2N aqueous HCl and EtOAc, the organic layer was separated, washed with $H_2O$, dried over $MgSO_4$ and evaporated. The crude product was purified on silica gel, eluting with $CH_2Cl_2$/MeOH (97/3, v/v) to afford the subtitle compound as a colourless solid (2.94 g, 39%). $R_f$ 0.68 ($CH_2Cl_2$/MeOH 95/5, v/v). MS m/z 366 ($MNH_4^+$).

(c) 6-Amino-3-ethoxy-2-iodo-4-methylbenzonitrile

The subtitle compound was prepared by the method of Example 1(e) from the product of step (b). The product was purified on silica gel, eluting with $CH_2Cl_2$/MeOH (98/2, v/v) to afford the subtitle compound (72%) as a colourless solid. $R_f$ 0.11 ($CH_2Cl_2$/MeOH 95/5, v/v). MS m/z 336 ($MNH_4^+$).

(d) 3-Ethoxy-2-iodo-6-[1-(5-methanesulfonamido-1.2,3,4-tetrahydroisoquinol-2-yl)ethylideneamino]-4-methylbenzonitrile The subtitle compound was prepared by the method of Example 1(f) from the product of step (c) and the compound of Example 22(a). The product was purified on silica gel, eluting with $CH_2Cl_2$/MeOH (98/2, v/v) to afford the subtitle compound (53%) as a colourless foam. $R_f$ 0.14 ($CH_2Cl_2$/MeOH 95/5, v/v). MS m/z 569 (MH+).

(e) 3-Ethoxy-6-[1-(5-methanesulfonamido-1.2,3,4-tetrahydroisoquinol-2-yl)ethylideneamino]-4-methoxy-2-(2-pyridyl)benzonitrile The subtitle compound was prepared by the method of Example 5 from the product of step (d) and 2-(tri-n-butylstannyl)pyridine. The product was purified on silica gel, eluting with $CH_2Cl_2$/MeOH (94/6, v/v) to give the subtitle compound (54%) as a foam. $R_f$ 0.14 ($CH_2Cl_2$/MeOH 95/5, v/v). MS m/z 520 (MH+).

(f) 4-Amino-6-ethoxy-2-(5-methanesulfonamido-1,2,3,4-tetrahydroisoquinol-2-yl)-7-methoxy-5-(2-pyridyl)quinoline A solution of the product of step (e) (1.14 g, 2.19 mmol) in THF (10 ml) was cooled to −78° C. and treated with a solution of lithium diisopropylamide in cyclohexane (1.5M, 4.4 ml, 6.6 mmol). The reaction was then allowed to reach room temperature over 1 h, partitioned between EtOAc and $H_2O$ and the aqueous layer extracted with 3 further portions of EtOAc. The combined organic layers were washed with brine, dried over $MgSO_4$ and evaporated under reduced pressure. Purification on silica gel, eluting with $CH_2Cl_2$/MeOH/0.88$NH_3$ (93/7/1, v/v) followed by trituration with ether afforded the title compound as a colourless foam (510 mg, 45%). $R_f$ 0.23 ($CH_2Cl_2$/MeOH/0.88$NH_3$ 90/10/1, v/v). MS m/z 520 (MH+). $^1$H NMR ($CDCl_3$) δ: 0.92 (3H, t), 2.84 (2H, m), 3.00 (3H, s), 3.82 (4H, m), 3.98 (3H, s), 4.22 (2H, q), 4.77 (2H, s), 5.93 (1H, s), 7.07 (1H, m), 7.17 (1H, t), 7.20–7.35 (2H, m), 7.40 (1H, t), 7.50 (1H, d), 7.81 (1H, t), 7.46 (1H, d), 8.77 (1H, d). Found: C,60.32; H,5.66; N,12.60 $C_{27}H_{29}N_5O_4S$ 0.25.$CH_2Cl_2$ requires C,60.51; H,5.50; N,12.95%.

EXAMPLE 24

4-Amino-6,7-dimethoxy-5-(2-pyridyl)-2-(5,6,7,8-tetrahydro-1,6-naphthyrid-6-yl)quinoline (a) 6-Acetyl-5,6,7,8-tetrahydro-1,6-naphthyridine To a solution of 5,6,7,8-tetrahydro-1,6-naphthyridine (4.9 g, 36.5 mmol) in $CH_2Cl_2$ at 0° C. was added triethylamine (6.1 ml, 43.8 mmol) and acetyl chloride (3.11 ml, 43.8 mmol) dropwise and the reaction was allowed to warm to room temperature and stirred for a further 18 h. The reaction mixture was partitioned between $H_2O$ and $CH_2Cl_2$, the layers were separated and the aqueous layer was extracted twice more with $CH_2Cl_2$. The combined organic layers were dried over $MgSO_4$ and evaporated under reduced pressure to afford a residue which was purified on silica gel, eluting with EtOAc/MeOH/0.88$NH_3$ (95/5/1, v/v). This afforded the subtitle compound (58%) as an oil. $R_f$ 0.60 ($CH_2Cl_2$/MeOH/0.88$NH_3$ 84/14/2, v/v). $^1$H NMR ($CDCl_3$) δ: 2.15 (3H, s), 3.04 (2H, m), 3.75 and 3.90 (2H, 2×m), 4.60 and 4.70 (2H, 2×s), 7.10 (1H, m), 7.42 (1H, m), 8.42 (1H, m).

(b) 3,4-Dimethoxy-2-iodo-6-[1-(5,6,7,8-tetrahydro-1 6-naphthyrid-6-yl)ethylideneamino]benzonitrile The subtitle compound was prepared by the method of Example 1(f) from the product of step (a) and the compound of Example 1(e). The product was purified on silica gel, eluting with EtOAc/MeOH (95/5, v/v) to afford the subtitle compound (80%) as a pale yellow solid. $R_f$ 0.58 ($CH_2Cl_2$/MeOH/0.88$NH_3$ 92/7/1, v/v). MS m/z 463 (MH+).

(c) 3,4-Dimethoxy-2-(2-pyridyl)-6-[1 -(5,6,78-tetrahydro-1.6-naphthyrid-6-yl)ethylideneamino]benzonitrile The subtitle compound was prepared by the method of Example 5 from the product of step (b) and 2-(tri-n-butylstannyl)pyridine. The product was purified on silica gel, eluting with EtOAc/MeOH/0.88$NH_3$ (95/5/1, v/v) to give the subtitle compound (51%) as a foam. $R_f$ 0.26 (EtOAc/MeOH/0.88NH$_3$ 90/10/1, v/v). MS m/z 414 (MH$^+$).

(d) 4-Amino-6,7-dimethoxy-5-(2-pyridyl)-2-(5,6,7,8-tetrahydro-1,6-naphthyrid-6-yl)quinoline The title compound was prepared by the method of Example 23(f) from the product of step (c). The product was purified on silica gel, eluting with CH$_2$Cl$_2$/MeOH/0.88NH$_3$ (96/3.5/0.5, v/v) followed by trituration with ether to afford the title compound (22%) as a light brown solid. $R_f$ 0.31 (CH$_2$Cl$_2$/MeOH/0.88NH$_3$ 92/7/1, v/v). MS m/z 414 (MH$^+$). $^1$H NMR (CDCl$_3$) δ: 3.13 (2H, m), 3.52 (3H, s), 3.82 (2H, bs), 3.98 (5H, m), 4.83 (2H, s), 5.98 (1H, s), 7.13 (1H, m), 7.22 (1H, bs), 7.38 (1H, m), 7.48 (1H, d), 7.53 (1H, m), 7.80 (1H m), 8.43 (1H, d), 8.76 (1H, d). Found: C,67.74; H,6.26; N,15.43 C$_{24}$H$_{23}$N$_5$O$_2$S 0.4.ether 0.6.H$_2$O requires C,67.86; H,6.07; N,15.33%.

EXAMPLE 25

4-Amino-6,7-dimethoxy-5-(2-pyrimidyl)-2-(5,6,7,8-tetrahydro-1.6-naphthyrid-6-yl)quinoline (a) 3,4-Dimethoxy-2-pyrimidyl-6-[1-(5,6,7,8-tetrahydro-1,6-naphthyrid-6-yl)ethylideneamino]benzonitrile The subtitle compound was prepared by the method of Example 5 from the product of Example 24(b) and 2-(tri-n-butylstannyl)pyrimidine. The product was purified on silica gel, eluting with CH$_2$Cl$_2$/MeOH (98/2, v/v) to give the subtitle compound as a foam (75%). $R_f$ 0.21 (ether). MS m/z 415 (MH$^+$).

(b) 4-Amino-6,7-dimethoxy-5-(2-pyrimidyl)-2-(5,6,7,8-tetrahydro-16-naphthyrid-6-yl)quinoline Potassium hydroxide powder (72 mg, 1.29 mmol) was added to a solution of the product of step (a) (530 mg, 1.28 mmol) in DMSO (5 ml). The reaction mixture was heated to 95° C. for 45 min. After cooling the reaction mixture was poured into citric acid and basified with 2N aqueous NaOH. The product was then extracted with EtOAc (×4). The combined organic layers were washed with H$_2$O, saturated brine and dried over MgSO$_4$. The product was purified on silica gel, eluting with CH$_2$Cl$_2$/MeOH/0.88NH$_3$ (96/3.5/0.5, v/v). The product was triturated with ether to afford the title compound as an orange solid (91 mg, 17%). $R_f$ 0.11 CH$_2$Cl$_2$/MeOH (95/5, v/v). MS m/z 415 (MH$^+$). $^1$H NMR (CDCl$_3$), δ: 3.10 (2H, t), 3.69 (3H, s), 3.79 (2H, s), 4.00 (2H, m), 4.05 (3H, s), 4.82 (2H, s), 6.01 (1H,s), 7.05 (1H, m), 7.40 (1H, t), 7.50 (1H, m), 8.40 (1H, m), 8.90 (2H, m).

EXAMPLE 26

4-Amino-7-methoxy-2-[4-(4-morpholinecarbonyl)-1,4-diazepan-1-yl]-5-(2-pyridyl)-6-(2,2,2-trifluoroethoxy)quinoline (a) 3-Hydroxy-4-methoxy benzoic acid, methyl ester To a suspension of 3-hydroxy-4-methoxy benzoic acid (33.63 g, 0.2 mol) in MeOH (500 ml) was added concentrated sulphuric acid (25 ml) and the reaction mixture was heated to reflux for 2 h. On cooling the reaction mixture was concentrated under reduced pressure to 100 ml and the residue was extracted with EtOAc. The organic layer was washed sequentially with H$_2$O (×2), saturated aqueous sodium bicarbonate and saturated brine, dried over MgSO$_4$ and evaporated under reduced pressure, to afford the subtitle compound as colourless crystals (33.0 g, 91%). $R_f$ 0.59 (EtOAc). MS m/z 183 (MH$^+$).

(b) 2,2,2-Trifluoroethyl trifluoromethanesulfonate.

To a solution of trifluoromethanesulfonic anhydride (80.4 g, 0.3 mol) in CH$_2$Cl$_2$ (50 ml) was added a mixture of 2,2,2-trifluoroethanol (28.0 g, 0.28 mol) and triethylamine (29.3 g, 0.29 mol) at −40° C. dropwise over 45 min. After addition, the reaction mixture was warmed to room temperature, washed sequentially with H$_2$O and saturated aqueous sodium bicarbonate and then dried over MgSO$_4$. This afforded the subtitle compound as a solution in CH$_2$Cl$_2$ which was used immediately in the next step.

(c) 4-Methoxy-3-(2,2,2-trifluoroethoxy)benzoic acid, methyl ester

To a solution of the product of step (a) (33.0g, 0.181 mol) in a mixture of potassium carbonate (41.4 g, 0.3 mol) and DMF (100 ml) was added a solution of the product obtained from step (b) (65.0 g, 0.28 mol). The reaction mixture was stirred at room temperature for 18 h after which time the reaction mixture was evaporated under reduced pressure. The residue was partitioned between ether and H$_2$O the organic layer was washed with saturated brine, dried over MgSO$_4$ and evaporated under reduced pressure. The crude product was triturated with hexane to afford the subtitle compound as a colourless solid (42.55 g, 93% over 2 steps). $R_f$ 0.47 (CH$_2$Cl$_2$). MS m/z 265 (MH$^+$).

(d) 4-Methoxy-3-(2,2,2-trifluoroethoxy)benzoic acid

To a solution of the product of step (c) (42.25g, 0.16 mol) in MeOH was added 2N aqueous NaOH (160 ml, 0.32 mol). The reaction mixture was stirred at room temperature for 3 h and then at 50° C. for 1 h. After cooling the reaction mixture was evaporated under reduced pressure. The residue was partitioned between EtOAc and 2N HCl, the organic layer dried over MgSO$_4$ and evaporated under reduced pressure to afford the subtitle compound as a colourless solid (40.4 g, 100%). $R_f$ 0.13 (hexane/EtOAc 1/1, v/v). MS m/z 251 (MH$^+$).

(e) 4,4-Dimethyl-2-[4-methoxy-3-(2,2,2-trifluoroethoxy)phenyl]-Δ$^2$-oxazoline

To a suspension of the product of step (d) (40.0 g, 0.16 mol) in CH$_2$Cl$_2$ (200 ml) and DMF (0.5 ml) was added oxalyl chloride (40.6 g, 0.32 mol) at 0° C. over a period of 15 min. The reaction mixture was stirred at 0° C. for 30 min, warmed to room temperature over 1.5 h and evaporated under reduced pressure. The residue was then redissolved in CH$_2$Cl$_2$ (300 ml) and added over 15 min to a solution of 2-amino-2-methylpropanol (17.8 g, 0.2 mol) and triethylamine (20.2 g, 0.2 mol) in CH$_2$Cl$_2$ (100 ml) at 0° C. The reaction mixture was then stirred at room temperature for 30 min, washed sequentially with 5% citric acid and dilute aqueous sodium bicarbonate, dried over MgSO$_4$ and evaporated under reduced pressure to a volume of 200 ml. Thionyl chloride (21.4 g, 0.18 mol) was added dropwise to the solution and the resulting mixture was stirred for 1 h. The product was then extracted with H$_2$O followed by 0.5N aqueous NaOH. The combined aqueous phases were basified with 2N aqueous NaOH and the product extracted with CH$_2$Cl$_2$(×2). The combined organic phases were dried over MgSO$_4$ and evaporated under reduced pressure to afford a batch of crude product. The original organic extract was then shaken with 2N aqueous NaOH and the product extracted with CH$_2$Cl$_2$ (×3), the combined organic extracts were dried over MgSO$_4$ and evaporated under reduced pressure. The residue was redissolved in ethereal HCl (150 ml), the resulting white solid was filtered off, rebasified with 2N aqueous NaOH and extracted with CH$_2$Cl$_2$ (×3). The combined organic extracts were dried over MgSO$_4$ and evaporated under reduced pressure to afford a second batch of crude product. The combined crude products were purified on silica gel eluting with CH$_2$Cl$_2$/MeOH (95/5, v/v) to afford the subtitle compound as a colourless solid (38.8 g, 80%). $R_f$ 0.54 (EtOAc). MS m/z 304 (MH$^+$).

(f) 4,4-Dimethyl-2-[2-iodo-4-methoxy-3-(2,2,2-trifluoroethoxy)phenyl]-Δ$^2$-oxazoline The subtitle compound was prepared by the method of Example 1(b) from the product of step (e). The crude product was purified on silica gel eluting with EtOAc/hexane (60/40, v/v). The product was then triturated with ether to afford the subtitle compound as an orange solid (53%). $R_f$ 0.27 (ether/hexane 1/3, v/v). MS m/z 430 (MH$^+$).

(g) 2-Iodo-4-methoxy-3-(2,2,2-trifluoroethoxy)benzonitrile

The subtitle compound was prepared by the method of Example 1(c) from the product of step (f). The crude product was triturated with hexane/ether (60/40, v/v) to afford the subtitle compound as a colourless solid (96%). $R_f$ 0.5 (EtOAc/hexane 1/1, v/v). MS m/z 358 (MH$^+$).

(h) 2-Iodo-4-methoxy-6-nitro-3-(2,2,2-trifluoroethoxy)benzonitrile

The subtitle compound was prepared by the method of Example 1(d) from the product of step (g). The crude brown solid was triturated with ether to afford the subtitle compound (72%). $R_f$ 0.25 (hexane/EtOAc 2/1, v/v). MS m/z 403 (MH$^+$).

(i) 6-Amino-2-iodo-4-methoxy-3-(2,2,2-trifluoroethoxy)benzonitrile

The subtitle compound was prepared by the method of Example 1(e) from the product of step (h). The crude product was washed though a plug of silica gel to afford the subtitle compound as an orange solid (70%). $R_f$ 0.74 (CH$_2$Cl$_2$/MeOH/0.88NH$_3$ 93/7/1, v/v). MS m/z 373 (MH$^+$).

(j) 2-Iodo-4-methoxy-6-{1-[4-(4-morpholinecarbonyl)-1,4-diazepan-1-yl]ethylideneamino}-3-(2,2,2-trifluoroethoxy)benzonitrile The subtitle compound was prepared by the method of Example 1(f) from the product of step (i) and Intermediate 4. The crude product was purified on silica gel eluting with CH$_2$Cl$_2$/MeOH (90/10, v/v) to afford the subtitle compound as an orange oil which was recrystallised from EtOAc to yield a colourless solid (64%). $R_f$ 0.12 (EtOAc). MS m/z 610 (MH$^+$).

(k) 4-Methoxy-6-{1-[4-(4-morpholinecarbonyl)-1,4-diazepan-1-yl]ethylideneamino}-2-(2-pyridyl)-3-(2,2,2-trifluoroethoxy)benzonitrile The subtitle compound was prepared by the method of Example 5 from the product of step (j)and 2-(tri-n-butylstannyl)pyridine. The crude product was purified on silica gel eluting with CH$_2$Cl$_2$/MeOH (96/4, v/v) to afford the subtitle compound as a yellow foam (91%). $R_f$ 0.43 (CH$_2$Cl$_2$/MeOH/0.88NH$_3$ 93/7/1, v/v). MS m/z 561 (MH$^+$).

(l) 4-Amino-7-methoxy-2-[4-(4-morpholinecarbonyl)-1,4-diazepan-1yl]-5-(2-pyridyl)-6-(2,2,2-trifluoroethoxy)quinoline To a solution of the product of step (k) (0.56 g, 1 mmol) in THF (10 ml) was added freshly prepared lithium diisopropylamide (4 ml, 2 mmol) at −20° C. The reaction mixture was then warmed to room temperature slowly and stirred for 20 min, after which time it was quenched with H$_2$O and poured into EtOAc. The organic layer was then washed with 2N aqueous NaOH followed by saturated brine, dried over MgSO$_4$ and evaporated under reduced pressure. The crude product was purified on silica gel eluting with CH$_2$Cl$_2$/MeOH/0.88NH$_3$ (90/10/1, v/v) to afford the title compound as a brown foam (0.39 g, 70%). $R_f$ 0.37 (CH$_2$Cl$_2$/MeOH/0.88NH$_3$ 93/7/1, v/v). MS m/z 561 (MH$^+$). $^1$H NMR (CDCl$_3$) δ: 2.00 (2H, m), 3.10 (5H, m), 3.30 (2H, m), 3.50–3.90 (10H, m), 3.95 (3H, s), 4.00 (3H, s), 5.80 (1H,s), 7.10 (1H,bs), 7.39 (1H, m), 7.45 (1H, d), 7.80 (1H, m), 8.70 (1H, d). Found C,51.49; H,5.72; N,14.35; C$_{27}$H$_{31}$F$_3$N$_6$O$_4$ 0.33.EtOAc requires C, 51.69; H,5.71; N,14.35%.

EXAMPLE 27

4-Amino-7-methoxy-5-(2-pyrimidinyl)-2-(5,6,7,8-tetrahydro-1,6-naphthyrid-6-yl)-6-(2,2,2-trifluoroethoxy)quinoline (a) 2-Iodo-4-methoxy-6-[1-(5,6,7,8-tetrahydro-1,6-naphthyrid-6-yl)ethylideneamino]-3-(2,2,2-trifluoroethoxy)benzonitrile The subtitle compound was prepared by the method of Example 1(f) from the product of Example 26(i) and the compound of Example 24(a). The crude product was purified on silica gel eluting with EtOAc/MeOH (80/20, v/v) to afford the subtitle compound as a colourless foam (70%). $R_f$ 0.63 (CH$_2$Cl$_2$/MeOH/0.88NH$_3$ 90/10/1, v/v). MS m/z 531 (MH$^+$).

(b) 4-Methoxy-2-(2-pyrimidyl)-6-[1-(5,6,7,8-tetrahydro-1,6-naphthyrid-6 -yl)ethylideneamino]-3-(2,2,2-trifluoroethoxy)benzonitrile The subtitle compound was prepared by the method of Example 5 from the product of step (a) and 2-(tri-n-butylstannyl)pyrimidine. The crude product was purified on silica gel eluting with CH$_2$Cl$_2$/MeOH/0.88NH$_3$ (94/6/1, v/v) to afford the subtitle compound as a colourless solid (49%). $R_f$ 0.29 (CH$_2$Cl$_2$/MeOH/0.88NH$_3$ 93/7/1, v/v). MS m/z 483 (MH$^+$).

(c) 4-Amino-7-methoxy-5-(2-pyrimidinyl)-2-(5,6,7,8-tetrahydro-1,6-naphthyrid-6-yl)-6 -2,2,2-trifluoroethoxy)quinoline The title compound was prepared by the method of Example 25(b) from the product of step (b). The crude product was purified on silica gel eluting with CH$_2$Cl$_2$/MeOH (95/5, v/v) to afford the title compound as a foam (8%). $R_f$ 0.07 (CH$_2$Cl$_2$/MeOH 95/5, v/v). MS m/z 483 (MH$^+$). $^1$H NMR (CDCl$_3$) δ3.18 (2H, m), 3.80 (2H, bs), 4.00 (5H, m), 4.30 (2H, m), 4.90 (2H, s), 6.00 (1H, s), 7.10 (1H, m), 7.30 (1H, s), 7.40 (1H, m), 7.50 (1H, d), 8.40 (1H, d), 8.90 (2H, d).

EXAMPLE 28

4-Amino-6,7-dimethoxy-2-[4-(4-morpholinecarbonyl)-1,4-diazepan-1-yl]-5-(oxazol-2 -yl)quinoline To a solution of oxazole (276 mg, 4 mmol) in THF (15 ml) was added n-butyllithium (1.6M in hexane, 2.75 ml, 4.4 mmol) dropwise at −78° C. under a nitrogen atmosphere. The reaction mixture was stirred at −78° C. for 20 min, zinc chloride solution (1.0M in ether, 12 ml, 12 mmol) was then added to the reaction mixture and the resulting solution was warmed to room temperature. The compound of Example 1(f) (1.05 g, 1.94 mmol) was added followed by tetrakis (triphenylphosphine)palladium (200 mg). The reaction mixture was heated at reflux for 3 h. This was followed by the addition of a further portion of oxazole zincate, prepared as above using oxazole (552 mg, 8 mmol), n-butyllithium (1.6M in hexane, 5.5 ml, 8.8 mmol) and zinc chloride solution (1.0M in ether, 24 ml, 24 mmol) followed by tetrakis-(triphenylphosphine)palladium (100 mg). The reaction mixture was refluxed for 4 h after which time copper(I) iodide (100 mg) was added. The resulting mixture was refluxed for 24 h. The cooled reaction mixture was poured into EtOAc and washed with aqueous EDTA solution, basified with 2N aqueous NaOH and the organic layer was separated, washed with saturated brine, dried over MgSO$_4$ and evaporated under reduced pressure. The crude product was purified on silica gel eluting with CH$_2$Cl$_2$/MeOH/0.88NH$_3$ (92/8/1, v/v) to afford the title compound (87 mg, 9%). $R_f$ 0.46 (CH$_2$Cl$_2$/MeOH/0.88NH$_3$ 93/7/1, v/v). MS m/z 483 (MH$^+$). $^1$H NMR (CDCl$_3$) δ: 2.10 (2H, m), 3.10 (4H, m), 3.35 (2H, m), 3.50–3.90 (12H, several peaks), 3.95 (2H, m), 4.00 (3H, s), 4.20 (1H, bs), 5.85 (1H, s), 7.35 (1H, s), 7.70 (1H, m), 7.90 (1H, s).

EXAMPLE 29

4-Amino-6,7-dimethoxy-2-(2-methyl-5,6,7,8-tetrahydro-1,6-naphthyrid-6-yl)-5-(2-pyridyl)quinoline (a) 6-Acetyl-2-methyl-5,6,7,8-tetrahydro-1,6-naphthyridine To a solution of 2-methyl-5,6,7,8-tetrahydro-1,6-naphthyridine [Shiozawa et al., Chem. Pharm. Bull., 32, 2522, (1984)] (2.73 g, 0.0184 mol) in $CH_2Cl_2$ (30 ml) and triethylamine (5.1 ml, 0.0368 mol) was added acetyl chloride (1.57 ml, 0.0221 mol) at 0° C. The reaction mixture was stirred for 24 h at room temperature, after which time the reaction mixture was washed sequentially with saturated aqueous sodium bicarbonate, $H_2O$ saturated brine, dried over $MgSO_4$ and evaporated under reduced pressure to afford the subtitle compound (3.27 g, 93%). $R_f$ 0.5 ($CH_2Cl_2$/MeOH/0.88$NH_3$ 90/10/1, v/v). MS m/z 191 ($MH^+$).

(b) 3,4-Dimethoxy-2-iodo-6-[1-(2-methyl-5,6,7,8-tetrahydro-1,6-naphthyrid-6 -yl)ethylideneamino]benzonitrile The subtitle compound was prepared by the method of Example 1(f) from the product of step (a) and the compound of Example 1(e). The crude product was purified on silica gel eluting with EtOAc/hexane (96/4, v/v) to afford the subtitle compound as a foam (87%). $R_f$ 0.42 (EtOAc). MS m/z 477 ($MH^+$).

(c) 3,4-Dimethoxy-6-[1-(2-methyl-5,6,7,8-tetrahydro-1,6-naphthyrid-6-yl)ethylideneamino]-2-(2-pyridyl)benzonitrile The subtitle compound was prepared by the method of Example 5 from the compound of step (b) and 2-(tri-n-butylstannyl)pyridine. The crude product was purified on silica gel eluting with EtOAc/MeOH (97/3, v/v) to afford the subtitle compound as a foam (25%). $R_f$ 0.29 (EtOAc). MS m/z 428 ($MH^+$).

(d) 4-Amino-6,7-dimethoxy-2-(2-methyl-5,6,7,8-tetrahydro-1,6-naphthyrid-6-yl)-5-(2pyridyl)quinoline The title compound was prepared by the method of Example 26(l) from the product of step (c). The crude product was purified on silica gel eluting with $CH_2Cl_2$/MeOH/0.88$NH_3$ (93/7/1, v/v) to afford the title compound as a foam (10%). $R_f$ 0.25 ($CH_2Cl_2$/MeOH/0.88$NH_3$, 90/10/1, v/v). MS m/z 233 ($MH^+$). $^1H$ NMR ($CDCl_3$) δ: 1.30 (2H, bs), 2.50 (3H, s), 3.10 (2H, m) 3.59 (3H, s), 3.85 (2H, m), 3.95–4.00 (6 H, m), 4.80 (2H, s), 6.00 (1H, s), 7.00 (1H, d), 7.20 (1H, s), 7.40 (1H, m), 7.45 (1H, m), 7.80 (1H, m), 8.75 (1H, m).

EXAMPLE 30

4-Amino-6,7-dimethoxy-2-(5-methoxy-1,2,3,4-tetrahydroisoquinol-2-yl)-5-(2-pyridyl)quinoline (a) 5-Methoxyisoquinoline To a solution of 5-hydroxyisoquinoline (10 g, 69 mmol) in MeOH (100 ml) was added a solution of sodium methoxide in methanol (30% by weight, 13.8 ml, 72.4 mmol) followed by phenyltrimethylammonium chloride (12.4 g, 72.4 mmol). The reaction mixture was stirred at room temperature for 2 h, after which time it was filtered and the filtrate evaporated under reduced pressure to afford an oil which was dissolved in DMF (50 ml). The reaction mixture was refluxed for 2 h after which time the reaction mixture was evaporated under reduced pressure. The resulting oil was partitioned between $CH_2Cl_2$ and 1N aqueous NaOH, the organic layer was washed twice with 1N aqueous NaOH, dried over $MgSO_4$ and evaporated under reduced pressure. The crude product was purified on silica gel eluting with EtOAc/hexane (1/1, v/v) to afford the subtitle compound as a yellow oil (6.1 g, 56%). $^1H$ NMR ($CDCl_3$) δ: 4.05 (3H, s), 7.00 (1H, d), 7.55 (2H, m), 8.02 (1H, d), 8.55 (1H, d), 9.22 (1H, s).

(b) 5-Methoxy-1,2,3,4-tetrahydroisoquinoline

To a solution of the product of step (a) (6.11 g, 384 mmol) in EtOH (200 ml) was added platinum oxide (0.611 g) followed by concentrated HCl (3.2 ml, 38.4 mmol). The reaction mixture was hydrogenated at 345 kPa (50 p.s.i.) at room temperature for 4 h after which time the catalyst was filtered off and washed with EtOH. The filtrate was evaporated under reduced pressure to afford the subtitle compound as a colourless solid (7.27 g, 95%). $^1H$ NMR ($D_6$-DMSO) δ: 2.80 (2H, m), 3.35 (2H, m), 3.80 (3H, s), 4.20 (2H, s), 6.80 (1H, d), 6.90 (1H, d), 7.20 (1H, t), 9.45 (2H; bs).

(c) 2-Acetyl-5-methoxy-1,2,3,4-tetrahydroisoquinoline

To a solution of the product of step (b) (6.26 g, 31.4 mmol) and triethylamine (9.6 ml, 69.0 mmol) in $CH_2Cl_2$ (150 ml) was added acetyl chloride (2.7 ml, 37.7 mmol) at 0° C. over a period of 15 min. The reaction mixture was stirred at room temperature for 18 h after which time the solution was washed sequentially with $H_2O$ and saturated aqueous sodium bicarbonate solution, dried over $MgSO_4$ and evaporated under reduced pressure. The crude product was purified on silica gel eluting with EtOAc to afford the subtitle compound as an orange oil (6.07 g, 94%). $R_f$ 0.65 ($CH_2Cl_2$/MeOH/0.88$NH_3$ 90/10/1, v/v). MS m/s 206 ($MH^+$).

(d) 3,4-Dimethoxy-2-iodo-6-[1-(5-methoxy-1,2,3,4-tetrahydroisoquinol-2-yl)ethylideneamino ]benzonitrile The subtitle compound was prepared by the method of Example 1(f) from the product of step (c) and the compound of Example 1(e). The crude product was purified on silica gel eluting with $CH_2Cl_2$ to afford the subtitle compound as orange crystals (69%). $R_f$ 0.77 ($CH_2Cl_2$/MeOH 95/5, v/v). MS m/z 492 ($MH^+$).

(e) 3,4-Dimethoxy-6-[1-(5-methoxy-1,2,3,4-tetrahydroisoquinol-2-yl)ethylideneamino]-2-(2-pyridyl)benzonitrile The subtitle compound was prepared by the method of Example 5 from the product of step (d) and 2-(tri-n-butylstannyl)pyridine. The crude product was purified on silica gel eluting with ether to afford the subtitle compound as a colourless solid (62%). $R_f$ 0.73 ($CH_2Cl_2$/MeOH 90/10, v/v). MS m/z 443 ($MH^+$).

(f) 4-Amino-6,7-dimethoxy-2-(5-methoxy-1,2,3,4-tetrahydroisoquinol-2-yl)-5-(2 -pyridyl)quinoline The title compound was prepared by the method of Example 25(b) from the product of step (e). The crude product was purified on silica gel eluting with $CH_2Cl_2$/MeOH (95/5, v/v) to afford the title compound as a colourless solid (10%). $R_f$ 0.5 ($CH_2Cl_2$/MeOH 90/10, v/v). MS m/z 443 ($MH^+$). $^1H$ NMR ($CDCl_3$) δ: 2.90 (2H, t), 3.55 (3H, s), 3.75–3.90 (7H, m), 4.00 (3H, s), 4.79 (2H, s), 5.95 (1H, bs), 6.70 (1H, d), 6.85 (1H, d), 7.19 (1 H, t), 7.25 (1H, s), 7.39 (1H, t), 7.45 (1H, d), 7.80 (1H, t), 8.75 (1H, d). Found C,68.58; H,5.93 ; N,12.66; $C_{26}H_{26}N_4O_3$ 0.2.ether 0.6.$H_2O$ requires C, 68.76; H,6.29; N,11.97%.

EXAMPLE 31

4-Amino-6,7-dimethoxy-2-(6,7-dimethoxy-1,2,3,4-tetrahydroisoquinol-2-yl)-5-(2 -pyrimidyl)quinoline (a) 2-Acetyl-6,7-dimethoxy-1,2,3,4-tetrahydroisoquinoline The subtitle compound was prepared by the method of Example 30(c) from 6,7-dimethoxy-1,2,3,4-tetrahydroisoquinoline. The crude product was purified on silica gel eluting with EtOAc to afford the subtitle compound as a colourless solid (99%). $R_f$ 0.15 (EtOAc). $^1H$ NMR ($d_6$-DMSO) δ: 2.05 (3H, s), 2.60–2.80 (2H, d), 3.55 (2H, m), 3.65 (6H, s), 4.25 (2H, d), 6.70 (2 h, d).

b) 3,4-Dimethoxy-6-[1 -(6,7-dimethoxy-1,2,3,4-tetrahydroisoquinol-2-yl)ethylidene-amino]-2-iodobenzonitrile The subtitle compound was prepared by the method of Example 1(f) from the product of step (a) and the compound of Example 1(e). The crude product was purified on silica gel eluting with $CH_2Cl_2$ to afford the subtitle compound (71%). $R_f$ 0.74 (EtOAc). MS m/z 522 (MH$^+$).

(c) 3,4-Dimethoxy-6-[1-(6,7-dimethoxy-1,2,3,4-tetrahydroisoquinol-2-yl)ethylidene-amino]-2-(2-pyrimidyl)benzonitrile The subtitle compound was prepared by the method of Example 5 from the product of step (b) and 2-(tri-n-butylstannyl)pyrimidine. Purification on silica gel afforded the subtitle compound (33%). $R_f$ 0.38 (EtOAc). MS m/z 474 (MH$^+$).

(d) 4-Amino-6,7-dimethoxy-2-(6,7-dimethoxy-1,2,3,4-tetrahydroisoquinol-2-yl)-5-(2-pyrimidyl)quinoline The title compound was prepared by the method of Example 26(1) from the product of step (c). The crude product was purified on silica gel eluting with $CH_2Cl_2$/MeOH/0.88NH$_3$ (95/5/0.5, v/v) to afford the title compound as a foam (29%). $R_f$ 0.16 ($CH_2Cl_2$/MeOH 95/5, v/v). MS m/z 474 (MH$^+$). $^1$H NMR (CDCl$_3$) δ: 2.90 (2H, m), 3.70 (5H, s), 3.90 (9H, m), 4.00 (3H, s), 4.75 (2H, s), 6.65 (1H, s), 6.75 (1H,s), 7.20 (1H, s), 7.40 (1H, t), 8.95 (2H, m).

EXAMPLE 32

4-Amino-6,7-dimethoxy-2-(6,7-dimethoxy-1,2,3,4-tetrahydroisoquinol-2-yl)-5-(2 -pyridyl)-quinoline (a) 4-Amino-6,7-dimethoxy-2-(6,7-dimethoxy-1,2,3,4-tetrahydroisoquinol-2-yl)-5-iodoquinoline The subtitle compound was prepared by the method of Example 1(g) from the compound of Example 31(b). The crude product was purified on silica gel eluting with EtOAc/hexane (1/1, v/v) then with EtOAc to afford the subtitle compound as an off-white solid (67%). $R_f$ 0.5 (EtOAc). MS m/z 522 (MH$^+$).

(b) 4-Amino-6,7-dimethoxy-2-(6,7-dimethoxy-1,2,3,4-tetrahydroisoquinol-2-yl)-5-(2-pyridyl)quinoline The title compound was prepared by the method of Example 5 from the product of step (a) and 2-(tri-n-butylstannyl)pyridine. The crude product was purified on silica gel eluting with $CH_2Cl_2$/MeOH/0.88NH$_3$ (95/5/0.5, v/v) to afford the title compound (20%). $R_f$ 0.28 ($CH_2Cl_2$/MeOH 95/5, v/v). MS m/z 473 (MH$^+$). $^1$H NMR (CDCl$_3$) δ: 2.85 (2H, t), 3.50 (3H, s), 3.70–3.90 (10H, m), 4.00 (3H, s), 4.70 (2H, s), 5.95 (1H, s), 6.65 (1H, s), 6.70 (1H, s), 7.20 (1H, s), 7.35 (1H, t), 7.45 (1H, d), 7.80 (1H, d), 8.75 (1H, d).

EXAMPLE 33

4-Amino-6,7-dimethoxy-2-[2-(4-morpholino)-5,6,7,8-tetrahydro-1,6-naphthyrid-6-yl]-5-(2-pyridyl) quinazoline (a) 6-Benzyl-3,4,5,6,7,8-hexahydro-1,6-naphthyridin-2-one To a solution of 1-benzyl-4-piperidone (213 g, 1.13 mol) in toluene (700 ml) was added pyrrolidine (190 ml, 2.25 mol), the reaction mixture was fitted with a Dean-Stark head and heated to 150° C. for 18 h. The reaction mixture was cooled and evaporated under reduced pressure, p-toluenesulphonic acid (4.0 g, 0.022 mol) was then added to the residue followed by acrylamide (160 g, 2.25 mol). The reaction mixture was heated with rapid stirring to 90° C. for 1.5 h and then for a further 2 h at 120° C. The cooled mixture was then filtered and the solid obtained washed with acetone followed by ether. The mother liquors were combined, evaporated under reduced pressure and the residue partitioned between EtOAc and H$_2$O. The organic layer was separated, dried over MgSO$_4$ and evaporated under reduced pressure to afford a further batch of solid. The solids were combined and heated to reflux with 4-toluenesulphonic acid (10 g, 0.056 mol) in dioxane (400 ml) for 18 h. On cooling, a colourless crystalline product was formed which was filtered and washed with EtOAc to afford the subtitle compound as colourless crystals (176 g, 65%). $R_f$ 0.1 (EtOAc). $^1$H NMR (CDCl$_3$) δ: 2.20 (4H, d), 2.50 (2H, t), 2.70 (2H, s), 3.00 (2H, s), 3.65 (2H, s), 7.20–7.45 (5H, m).

(b) 6-Benzyl-2-chloro-5,6,7,8-tetrahydro-1,6-naphthyridine

To a stirred suspension of the product of step (a) (30 g, 0.124 mol) in toluene (400 ml) was added phosphorous oxychloride (57.7 ml, 0.619 mol), followed by tetrachloro-1,4-benzoquinone (31.98 g, 0.13 mol). The reaction mixture was refluxed under nitrogen for 18 h after which time the toluene was evaporated under reduced pressure, the residue was then basified with 4N aqueous NaOH and the product extracted with ether (×3). The combined organic layers were dried over MgSO$_4$ and evaporated under reduced pressure. The crude product was purified on silica gel eluting with EtOAc to afford the subtitle compound as a solid (13.29 g, 41%). $R_f$ 0.8 (EtOAc). MS m/z 259 (MH$^+$).

(c) 2-Chloro-5,6,7,8-tetrahydro-1,6-naphthyridine

To a stirred solution of the product of step (b) (13.28 g, 0.0513 mol) in toluene (150 ml) was added 1-chloroethyl chloroformate (5.54 ml, 0.0513 mol) dropwise at 0° C. The reaction mixture was refluxed for 2 h. On cooling the toluene was evaporated under reduced pressure and the residue partitioned between EtOAc/H$_2$O, the organic layer was washed sequentially with 1N HCl and saturated brine, dried over MgSO$_4$ and evaporated under reduced pressure. The resulting residue was dissolved in MeOH (150 ml) and refluxed for 3 h after which time the reaction mixture was evaporated under reduced pressure and the residue was partitioned between $CH_2Cl_2$ and 2N aqueous NaOH and the product extracted with $CH_2Cl_2$ (×5). The combined organic layers were dried over MgSO$_4$ and evaporated under reduced pressure. The crude product was purified on silica gel eluting with $CH_2Cl_2$/MeOH/0.88NH$_3$ (90/10/1, v/v) to afford the subtitle compound (3.57 g, 41%). $R_f$ 0.25 ($CH_2Cl_2$/MeOH/0.88NH$_3$, 90/10/1, v/v). MS m/z 169 (MH$^+$).

(d) 2-Chloro-6-diphenylmethyl-5,6,7,8-tetrahydro-1,6-naphthyridine

To a solution of the product of step (c) (1.78 g, 0.01 mol) and triethylamine (2.21 ml, 0.016 mol) in $CH_2Cl_2$ (20 ml) was added diphenylchloromethane (2.13 ml, 0.012 mol). The reaction mixture was stirred at room temperature for 20 h and evaporated under reduced pressure. The residue was dissolved in DMA (20 ml) and heated to 100° C. for 18 h and once cooled, the solution was diluted with $CH_2Cl_2$ and washed sequentially with saturated aqueous sodium bicarbonate solution, H$_2$O and saturated brine then dried over MgSO$_4$. Evaporation under reduced pressure afforded the subtitle compound as a solid (1.01 g, 30%), $R_f$ 0.7 ($CH_2Cl_2$/MeOH/0.88NH$_3$ 90/10/1, v/v). MS m/z 335 (MH$^+$).

(e) 6-Diphenylmethyl-2-(4-morpholino)-5,6,7,8-tetrahydro-1,6-naphthyridine

To a solution of morpholine (0.62 ml, 7.17 mmol) in THF (15 ml) was added ethylmagnesium bromide (2.4 ml, 7.17 mmol) at 0° C., the reaction mixture was stirred for 1 h at room temperature after which time a solution of the product of step (d) (0.8 g, 2.389 mmol) in THF (15 ml) was added followed by palladium(II) acetylacetonate (0.073 g, 0.239 mmol) and triphenylphosphine (0.125 g, 0.478 mmol) and the reaction mixture was heated to 60° C. for 18 h. On cooling the solution was partitioned between EtOAc and saturated aqueous ammonium chloride solution, the organic layer was separated, washed sequentially with H$_2$O saturated brine, dried over MgSO$_4$ and evaporated under reduced pressure. The crude product was purified on silica gel eluting with CH$_2$Cl$_2$/MeOH (97/3, v/v) to afford the subtitle compound (0.81 g, 88%). R$_f$ 0.63 (CH$_2$Cl$_2$/MeOH 95/5, v/v). MS m/z 386 (MH$^+$).

(f) 2-(4-Morpholino)-5,6,7,8-tetrahydro-1,6-naphthyridine

To a solution of the product of step (e) (0.8 g, 2.08 mmol) in MeOH/1N HCl (10/1, v/v, 33 ml) was added 20% palladium hydroxide on carbon (0.2 g). The reaction mixture was hydrogenated at 345 kPa (50 p.s.i.) and 50° C. for 56 h after which time the catalyst was filtered off and washed with MeOH. The resulting solution was evaporated under reduced pressure and the residue partitioned between CH$_2$Cl$_2$ and saturated aqueous sodium bicarbonate solution. The product was extracted with CH$_2$Cl$_2$ (×8), the combined organic layers were dried over MgSO$_4$ and evaporated under reduced pressure. The crude product was purified on silica gel eluting with CH$_2$Cl$_2$/MeOH/0.88NH$_3$ (90/10/1, v/v) to afford the subtitle compound (0.13 g, 28%). R$_f$ 0.4 (CH$_2$Cl$_2$/MeOH/0.88NH$_3$ 90/10/1, v/v). MS m/z 220 (MH$^+$).

(g) 4-Amino-6,7-dimethoxy-2-[2-(4-morpholino)-5,6,7,8-tetrahydro-1,6-naphthyrid-6-yl]-5-(2-pyridyl)quinazoline The title compound was prepared by the method of Example 12(b) from the compound of Example 12(a) and the product of step (f). The crude product was purified on silica gel eluting with CH$_2$Cl$_2$/MeOH (95/5, v/v) to afford the title compound as a colourless foam (29%). R$_f$ 0.37 (CH$_2$Cl$_2$/MeOH/0.88NH$_3$ 90/10/1, v/v). MS m/z 450 (MH$^+$). $^1$H NMR (CDCl$_3$) δ: 1.30 (2H, s), 2.50 (3H, s), 3.10 (2H, m), 3.90–4.1(8H, several peaks), 4.80 (2H, s), 6.00 (1H, s), 7.00 (1H, d), 7.24 (1H, s), 7.40 (2H, m), 7.45 (1H, d), 7.80 (1H, t), 8.75 (1H, m).

EXAMPLE 34

4-Amino-6,7-dimethoxy-2-(5-methanesulfonamido-1,2,3,4-tetrahydroisoquinol-2-yl)-5-(2-pyridyl)quinoline (a) 3,4-Dimethoxy-6-[1-(5-methanesulfonamido-1,2,3,4-tetrahydroisoquinol-2-yl)ethylideneamino]-2-(2-pyridyl)benzonitrile The subtitle compound was prepared by the method of Example 5 from the compound of Example 22(b) and 2-(tri-n-butylstannyl)pyridine. The product was purified on silica gel, eluting with CH$_2$Cl$_2$/MeOH (95/5, v/v) to give the subtitle compound (45%) as a foam. R$_f$ 0.11 (CH$_2$Cl$_2$/MeOH 95/5, v/v).

(b) 4-Amino-6,7-dimethoxy-2-(5-methanesulfonamido-1,2,3,4-tetrahydroisoquinol-2-yl)-5-(2-pyridyl)quinoline hydrochloride The title compound was prepared by the method of Example 23(f) from the product of step (a). The product was purified on silica gel, eluting with CH$_2$Cl$_2$/MeOH/0.88NH$_3$ (90/10/1, v/v) followed by treatment with excess ethereal HCl to afford the title compound (10%) as a colourless solid. R$_f$ 0.21 (CH$_2$Cl$_2$/MeOH/0.88NH$_3$ 93/7/1, v/v). MS m/z 506 (MH$^+$). $^1$H NMR (d$_6$-DMSO) δ: 3.08 (2H, m), 3.48 (3H, s), 3.5–3.7 (5H, m), 3.80 (2H, m), 4.00 (3H, m), 4.78 (2H, s), 6.00 (1H, bs), 6.19 (1H, s), 7.20 (1H, t), 7.28 (2H, m), 7.60 (2H, m), 7.90 (1H, s), 8.01 (1H, t), 8.77 (1H, d), 12.04 (1H, s). Found C,50.91; H,5.46; N,10.89; C$_{26}$H$_{28}$ClN$_5$O$_4$S 0.8.CH$_2$Cl$_2$ H$_2$O requires C, 51.26; H,5.07; N,11.15%.

EXAMPLE 35

The compound of Example 28 was tested in the first screen described above ("Contractile responses of human prostate") and found to have a pA$_2$ value of 9.2.

What is claimed is:

1. A compound of formula I,

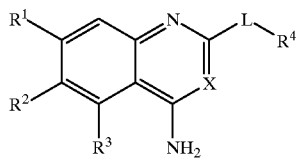

I wherein
R$^1$ represents C$_{1-4}$ alkoxy optionally substituted by one or more fluorine atoms;
R$^2$ represents H or C$_{1-6}$ alkoxy optionally substituted by one or more fluorine atoms;
R$^3$ represents a 5- or 6-membered heterocyclic ring containing at least one heteroatom selected from N, O and S, the ring being optionally substituted by one or more groups selected from halogen, C$_{1-4}$ alkoxy, C$_{1-4}$ alkyl and CF$_3$;
R$^4$ represents a 4-, 5-, 6-, or 7-membered heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, C$_{1-4}$ alkyl, C$_{1-4}$ alkoxy, halogen, CONR$^8$R$^9$, SO$_2$NR$^8$R$^9$, (CH$_2$)$_b$NR$^8$R$^9$ and NHSO$_2$(C$_{1-4}$ alkyl), and when S is a member of the ring system, it may be substituted by one or two oxygen atoms;
R$^8$ and R$^9$ independently represent H or C$_{1-4}$ alkyl, or together with the N atom to which they are attached they may represent a 5- or 6-membered heterocyclic ring containing at least one heteroatom selected from N, O and S;
b represents 0, 1, 2 or 3;
X represents N; and
L is absent, or represents a cyclic group of formula Ia,

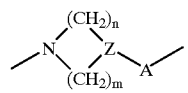

Ia in which N is attached to the 2-position of the quinoline or quinazoline ring;
A is absent or represents CO or SO$_2$;
Z represents CH or N;
m represents 1 or 2, and in addition, when Z represents CH, it may represent 0; and
n represents 1, 2 or 3, provided that the sum of m and n is 2, 3, 4 or 5;
or represents a chain of formula Ib,

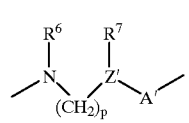

Ib in which N is attached to the 2-position of the quinoline or quinazoline ring;

A' and Z' have the same significance as A and Z above, respectively;

R$^6$ and R$^7$ independently represent H or C$_{1-4}$ alkyl; and p represents 1, 2 or 3, and in addition, when Z' represents CH, it may represent 0;

or a pharmaceutically acceptable salt thereof.

2. A compound as claimed in claim 1, wherein R$^1$ and R$^2$ each represent methoxy.

3. A compound as claimed in claim 1 or claim 2, wherein R$^3$ represents 2-pyridinyl or 2-pyrimidinyl.

4. A compound according to claims 1 or 2 wherein L is absent.

5. A compound according to claims 1 or 2, wherein R$^4$ comprises a saturated 6-membered N-containing ring which is fused to a benzene or pyridine ring.

6. A compound as claimed in claim 5, wherein the benzene ring is substituted by NHSO$_2$(C$_{1-4}$ alkyl).

7. A compound of formula I according to claim 1, or a pharmaceutically acceptable salt thereof, for use as a pharmaceutical.

8. The compound:

4-amino-6,7-dimethoxy-2-[4-(4-morpholinecarbonyl)-1,4-diazepan-1-yl]-5-(thiohen-3-yl)quinazoline;

4-amino-6,7-dimethoxy-2-[4-(4-morpholinecarbonyl)-1,4-diazepan-1-yl]-5-(3-pyridyl)quinazoline;

4-amino-6,7-dimethoxy-2-[4-(4-morpholinecarbonyl)-1,4-diazepan-1-yl]-5-(2-pyridyl)quinazoline;

4-amino-6,7-dimethoxy-5-(2-pyridyl)-2-(5,6,7,8-tetrahydro-1,6-maphthyrid-6-yl)quinazoline;

4-amino-6,7-dimethoxy-5-(2-pyrimidyl)-2-(5,6,7,8-tetrahydro-1,6-naphthyrid-6-yl)quinazoline;

4-amino-6,7-dimethoxy-5-(2-pyrimidyl)-2-(5,6,7,8-tetrahydro-1,3,6-triazanaphth-6-yl)quinazoline;

4-amino-2-(7-aminosulfonyl-1,2,3,4-tetrahydroisoquinol-2-yl)-6,7-dimethoxy-5-(2-pyridyl)quinazoline;

4-amino-6,7-dimethoxy-2-(2-isoindolinyl)-5-(b 2-pyridyl)quinazoline;

4-amino-6,7-dimethoxy-5-(2-pyridyl)-2-(5,6,7,8-tetrahydro-1,3,6-triazanaphth-6-yl)quinazoline;

4-amino-6,7-dimethoxy-2-(7-methanesulfonamido-2,3,4,5-tetrahydro-1H,3-benzazepin-3-yl)-5-(2-pyridyl)quinazoline;

4-amino-6,7-dimethoxy-2-(7-(4-morpholinesulfonamido)-1,2,3,4-tetrahydroisoquinolin-2-yl]-5-(2-pyridyl)quinazoline;

4-amino-6,7-dimethoxy-2-(2-methyl-5,6,7,8-tetrahydro-1,3,6-triazanaphth-6yl)-5-(2-pyridyl)quinazoline;

4-amino-6,7-dimethoxy-5-(2-pyridyl-2-(5,6,7,8-tetrahydro-1,3,7-triazanaphth-7-yl)quinazoline;

4-amino-6,7-dimethoxy-2-[7-(1-piperazinesulfonyl)-1,2,3,4-tetrahydroisoquinolin-2-yl]-5-(2-pyridyl)quinazoline;

4-amino-2-[5-(N,N-diethylaminomethyl)1,2,3,4-tetrahydroisoquinolin-2-yl]-6,7-dimethoxy-5-(2-pyridyl)quinazoline; or 4-amino-6,7-dimethoxy-2-[2-(4-morpholino-5,6,7,8-tetrahydro-1,6-naphthyrid-6-yl]-5-(2-pyridyl)quinazoline, or a pharmaceutically acceptable salt thereof.

9. The compound:

4-amino-6,7-dimethoxy-2-(5-methanesulfonamido-1,2,3,4-tetrahydroisoquinol-2-yl)- 5-(2-pyridyl)quinazoline, or a pharmaceutically acceptable salt thereof.

10. A pharmaceutical formulation including a compound of formula I, as defined in claim 1, or a pharmaceutically acceptable salt thereof, in admixture with a pharmaceutically acceptable adjuvant, diluent or carrier.

11. A method of treatment of benign prostatic hyperplasia which comprises administration of a compound of formula I, as defined in claim 1, or a pharmaceutically acceptable salt thereof, to a patient in need of such treatment.

* * * * *